(12) United States Patent
Flohr

(10) Patent No.: US 11,021,448 B2
(45) Date of Patent: Jun. 1, 2021

(54) 1,3-DIHYDRO-1,4-BENZODIAZEPINE-2-THIONES FOR THE TREATMENT OF CNS RELATED DISEASES

(71) Applicant: Hoffmann-La Roche Inc., Little Falls, NJ (US)

(72) Inventor: Alexander Flohr, Lörrach (DE)

(73) Assignee: Hoffmann-La Roche Inc., Little Falls, NJ (US)

( * ) Notice: Subject to any disclaimer, the term of this patent is extended or adjusted under 35 U.S.C. 154(b) by 0 days.

(21) Appl. No.: 16/399,134

(22) Filed: Apr. 30, 2019

(65) Prior Publication Data

US 2019/0256478 A1    Aug. 22, 2019

Related U.S. Application Data

(63) Continuation of application No. PCT/EP2017/077722, filed on Oct. 30, 2017.

(30) Foreign Application Priority Data

Nov. 1, 2016 (EP) .................................... 16196725

(51) Int. Cl.
| | |
|---|---|
| *C07D 243/24* | (2006.01) |
| *C07D 243/22* | (2006.01) |
| *C07D 401/04* | (2006.01) |
| *A61P 25/28* | (2006.01) |
| *A61P 25/18* | (2006.01) |

(52) U.S. Cl.
CPC ......... *C07D 243/24* (2013.01); *C07D 243/22* (2013.01); *C07D 401/04* (2013.01); *A61P 25/18* (2018.01); *A61P 25/28* (2018.01)

(58) Field of Classification Search
CPC .................................................. C07D 243/24
See application file for complete search history.

(56) References Cited

U.S. PATENT DOCUMENTS

| | | | | |
|---|---|---|---|---|
| 3,886,174 | A | * | 5/1975 | Hester, Jr. ..................... 540/563 |
| 3,917,627 | A | | 11/1975 | Hester, Jr. et al. |
| 3,987,052 | A | | 10/1976 | Hester, Jr. et al. |
| 4,031,078 | A | | 6/1977 | Szente et al. |
| 4,514,407 | A | | 4/1985 | Hester, Jr. et al. |
| 4,987,131 | A | | 1/1991 | Clemence et al. |
| 5,141,735 | A | * | 8/1992 | Bellemin ............. C07D 403/04 424/85.1 |
| 6,440,959 | B1 | * | 8/2002 | Ding .................... C07D 243/22 514/220 |

FOREIGN PATENT DOCUMENTS

| | | |
|---|---|---|
| DE | 2 237 592 A1 | 2/1973 |
| DE | 2 546 612 A1 | 4/1976 |
| DE | 2 546 614 A1 | 4/1976 |
| DE | 2546612 * | 4/1976 |
| EP | 0 227 539 A1 | 7/1987 |
| FR | 1 391 752 A | 2/1965 |
| GB | 1 472 487 | 5/1977 |
| WO | 01/90084 A1 | 11/2001 |
| WO | WO2003082832 * | 10/2003 |
| WO | 2010/059773 A1 | 5/2010 |
| WO | 2013/033246 A2 | 3/2013 |
| WO | 2016/171470 A1 | 10/2016 |

OTHER PUBLICATIONS

Hester et al., J'Med Med Chem. (1971).*
Bridges et al., "Chemical lead optimization of a pan Gq mAChR M1, M3, M5 positive allosteric modulator (PAM) lead. Part I: Development of the first highly selective M5 PAM" Bioorganic & Medicinal Chemistry Letters 20:558-562 ( 2010).
Bridges et al., "Chemical lead optimization of pan Gq MaChR M1, M3, M5 positive allosteric modulator (PAM) lead. Part II: Development of a potent and highly selective M1 PAM" Bioorganic & Medicinal Chemistry Letters 20:1972-1975 ( 2010).
Cremlyn et al., "some derivatives of morpholinophosphorodichloridate and dichloridothioate" J.Heterocyclic Chemistry 21:1457-64 ( 1984).
Digby et al., "Novel Allosteric Agonists of M1 Muscarinic Acetylcholine Receptors Induce Brain Region-Specific Responses That Correspond with Behavioral Effects of Animal Models" The Journal of Neuroscience 32(25):8535-8544 ( 2012).
International Search Report and Written Opinion for PCT/EP2017/077722 (dated Dec. 11, 2017).
Jones et al., "Novel Selective Allosteric Activator of the M1 Muscarinic Acetylcholine Receptor Regulates Amyloid Processing Produces Antipsychotic-Like Activity in Rats" The Journal of Neuroscience 28(41):10422-10433 (Oct. 2008).
Kennedy et al., "Synthesis and Structure-Activity Relationships of Allosteric Potentiators of the M4 Muscarinic Acetylcholine Receptor" ChemMedChem 4:1600-1607 ( 2009).
Kudak et al., "Quinolizidinone Carboxylic Acids as CNS Penetrant, Selective M1 Allosteric Muscarinic Receptor Modulators" ACS Medicinal Chemistry Letters 1:263-267 ( 2010).
Mahajan et al., "Meclonazepam analogues as potential new antihelmintic agents" Bioorganic & Medicinal Chemistry Letters 18(7):2333-2336 ( 2008).
Marlo et al., "Discovery and Characterization of Novel Allosteric Potentiators of M1 Muscarinic Receptors Reveals Multiple Modes of Activity" Molecular Pharmacology 75(8):577-588 ( 2009).
Meguro et al., "Heterocycles. VI. Synthese fo 4H-s-Triazolo [4, 3-a] [1, 4] benzodiazepines Novel Tricyclic Psychosedatives" Chemical and Pharmaceutical Bulletin 21(11):2382-2390 ( 1973).

(Continued)

*Primary Examiner* — Paul V Ward

(74) *Attorney, Agent, or Firm* — Mark D. Kafka

(57) ABSTRACT

The present invention provides compounds that are muscarinic M1 receptor positive allosteric modulators (PAM) and useful in the treatment of diseases, mediated by the muscarinic M1 receptor, such as Alzheimer's disease, cognitive impairment, schizophrenia, pain or sleep disorders, their manufacture, pharmaceutical compositions containing them and their use as therapeutically active substances.

4 Claims, No Drawings

(56) References Cited

OTHER PUBLICATIONS

Melancon et al., "Allosteric modulation of the M1 muscarinic acetylcholine receptor: improving cognition and a potential treatment for schizophrenia and Alzheimer's disease" Drug Discov Today 18 (Dec. 2013).

Melancon et al., "Isatin replacements applied to the highly selective, muscarinic M1 PAM ML137: Continued optimization of an MLPCN probe molecule" Bioorganic & Medicinal Chemistry Letters 23:412-416 ( 2013).

Poslusney et al., "Spirocyclic replacements for the isatin in the highly selective, muscarinic M1 PAM ML137: The continued optimization of an MLPCN probe molecule" Bioorganic & Medicinal Chemistry Letters 23:1860-1864 ( 2013).

Salovich et al., "Discovery of N-(4-methoxy-7-methylbenzo(d)thiazol-2-yl)isonicatinamide ML23, as a novel, selective and brain penetrant positive allosteric modulator of the muscarinic 4 (M4) receptor" Bioorganic & Medicinal Chemistry Letters 22:5084-5088 ( 2012).

Simonyi et al., "Conformational Recognition by Central Benzodiazepine Receptors" Bioorganic Chemistry 18:1-12 ( 1990).

Tarr et al., "Targeting Selective Activation of M1 for the Treatment of Alzheimer's Disease: Further Chemical Optimization and Pharmacological Characterization of the M1 Positive Allosteric Modulator ML 169" ACS Chemical Neuroscience 3:884-895 ( 2012).

Yu et al., "Design, Synthesis and Biological Evaluation of Sulfamide and Triazole Benzodiazepines as Novel p35-MDM2 Inhibitors" Int. J. Mol. Sci 15(9):15741-15753 ( 2014).

Flohr, A. et al., "Discovery of the first low-shift positive allosteric modulators for the muscarinic M1 receptor" Bioorganic & Medicinal Chemistry Letters 27(24):5415-5419 (Dec. 2017).

* cited by examiner

1,3-DIHYDRO-1,4-BENZODIAZEPINE-2-THIONES FOR THE TREATMENT OF CNS RELATED DISEASES

CROSS REFERENCE TO RELATED APPLICATIONS

This application is a continuation of International Application No. PCT/EP2017/077722, filed Oct. 30, 2017, which claims priority to EP Application No. 16196725.2, filed Nov. 1, 2016. The entire contents of each of the above patent applications are hereby incorporated by reference.

BACKGROUND ART

The muscarinic receptors (mAChRs) are members of the class A G-protein-coupled receptors. To date, five distinct subtypes of mAChRs (M1-M5) have been cloned and sequenced. The muscarinic M1 receptors are predominantly distributed in the brain, with the highest expression in the cortex, thalamus, striatum and hippocampus. In clinical studies, Xanomeline, a M1/M4-preferring agonist, demonstrated robust efficacy on positive, negative and cognitive symptoms in schizophrenic patients and improved cognitive scores and reduced psychotic-like behaviors in patients with Alzheimer's disease (AD). The M1 receptor has been implicated in memory and learning processes, regulation of dopamine and NMDA receptor activity and has thus been proposed as a potential target for the treatment of AD and schizophrenia.

AD is the most common cause of dementia in later life. Pathologically AD is characterized by the deposition in the brain of amyloid in extracellular plaques and intracellular neurofibrillary tangles. The amyloid plaques are mainly composed of amyloid peptides (Abeta peptides) which originate from the β-Amyloid Precursor Protein (APP) by a series of proteolytic cleavage steps. Several forms of APP have been identified of which the most abundant are proteins of 695, 751 and 770 amino acids length. They all arise from a single gene through differential splicing. The Abeta peptides are derived from the same domain of the APP but differ at their N- and C-termini, the main species are of 40 and 42 amino-acid length by processing of the beta-amyloid precursor protein (APP) by the beta-amyloid protein cleaving enzyme. The processing leads to accumulation of Abeta in the brain.

M1 receptors are abundantly expressed postsynaptically in cortex, hippocampus and striatum which are important brain regions involved for cognition. Based on the cholinergic hypothesis i.e. degeneration of presynaptic cholinergic nerve terminals in hippocampus and cortical regions, M1 activation should rescue the cognitive deficits which occur in AD, thus providing symptomatic treatment of this neurodegenerative disorder. Postmortem studies in AD cortical tissues have shown that M1 receptor expression are not reduced, thus providing evidence for target availability in a critical brain region. Moreover, preclinical studies have shown that M1 activation has potential as a disease-modifying therapy for AD by shifting the APP processing towards the non-amyloidogenic α-secretase pathway and by decreasing tau hyperphosphorylation. Therefore, M1 PAMs provide an approach to target both symptomatic and disease-modifying treatment of AD.

Schizophrenia is a severe, disabling, lifelong disorder that affects 1% of the population and is characterized by positive symptoms (such as hallucinations, delusions and paranoia), negative symptoms (such as social withdrawal and apathy) and cognitive impairment (for example, deficits in working memory, executive function and attention). Schizophrenia is a neurodevelopmental disorder with genetic risk factors and neuropathological changes. Aberrant activity occurs within the prefrontal-hippocampal-thalamic network in brains of schizophrenia patients. Positive symptoms of schizophrenia are suggested to be caused by dopaminergic system dysfunction, particularly increased dopamine activity within subcortical brain regions such as the striatum. Negative symptoms are thought to occur due to impaired signaling within the neurocircuitry of the ventral tegmental area and ventral striatum. Decreased NMDA receptor function in pyramidal neurons coupled with sub-optimal dopamine release in critical regions such as dorsolateral prefrontal cortex may account for some of the cognitive deficits.

M1 receptors are located in regions which are affected in schizophrenia, such as the hippocampus, cortex and striatum, in particular in the medium spiny neurons. Several reports have shown a reduction in muscarinic receptors in the prefrontal cortex and hippocampus, regions where M1 is densely expressed, in a subset of schizophrenic patients. Furthermore, preclinical studies have shown that M1 knockout mice have enhanced amphetamine-induced activity and increased striatal dopamine levels. Electrophysiology studies have revealed that activation of M1 receptors potentiates NMDA mediated hippocampal activity, modulates activity of medium spiny neurons and increases activity of medial prefrontal cortex neurons. Overall, activation of M1 receptors should modulate dysfunctional dopaminergic and glutamatergic signaling within the underlying neurocircuitry resulting in improvements in the symptoms of schizophrenia.

The clinical effects of Xanomeline and other muscarinic M1 agonist agents were however always associated with adverse effects attributed to their insufficient M1 muscarinic receptor subtype selectivity. The typical observed side effects, including sweating, salivation, gastrointestinal distress and bradycardia have been attributed to the non-specific activation of peripheral M2 and M3 mAChRs. Despite a tremendous effort from a number of companies, the search for highly M1 selective agonists has failed because of the high degree of conservation between muscarinic receptor subtypes at their orthosteric acetylcholine ligand binding sites.

To circumvent the selectivity and safety issues associated with targeting the highly conserved orthosteric ACh site, an alternative approach consists of developing M1 PAMs that act at the less highly conserved allosteric binding sites.

M1 PAMs from different chemical classes exhibiting, as rationalized, a good level of M1 subtype selectivity[1]. Importantly, similar to the preclinical profile of Xanomeline and other unselective M1 agonists, these M1 allosteric agents demonstrated pro-cognitive effects (in scopolamine-induced memory deficit in mice, scopolamine impaired non-human primates and in transgenic AD mice). PQCA and ML169 have been shown to promote non-amyloidogenic APP processing. Electrophysiology studies have shown that M1 PAMs potentiate carbachol-induced activity in the medial prefrontal cortex and medium spiny neurons. Moreover, unlike unselective agonists, M1 PAMs do not appear to produce side effects such as salivation at therapeutic effective doses. Additionally, they are expected to be devoid of liabilities such as receptor desensitization/internalization following chronic dosing previously reported for orthosteric receptor agonists. In summary, the PAM approach, by activating in a truly selective manner M1 receptors, is a highly promising novel strategy to deliver both efficacious and safe therapeutic agents for the treatment of schizophrenia (positive, negative and cognitive symptoms) as well as AD (symptomatic and disease modifying). Thus, the compounds of the invention, which are muscarinic M1 receptor positive allosteric modulators, are believed to be useful in the treatment of Alzheimer's disease and other diseases mediated by the muscarinic M1 receptor.

Simonyi et al[2]. investigate the influence of the substitution pattern at the C3 of the benzodiazepines on the GABA receptor and describe a preference of the M conformation of the ligand by the receptor.

U.S. Pat. No. 4,031,078[3] describes certain 1,4-benzodiazepin-2-thiones that could be used as anthelmintics. Meguro et al.[4] describe 1,4-benzodiazepins that are useful to treat depression. U.S. Pat. No. 4,514,407[5] describe 1,4-benzodiazepins as diuretics. U.S. Pat. No. 3,987,052[6] describe 1,4-benzodiazepins that can be used as tranquilizers.

The present invention provides novel compounds of formula I, their manufacture, medicaments based on a compound in accordance with the invention and their production as well as the use of compounds of formula I in the control or prevention of illnesses such as Alzheimer's disease, cognitive impairment, schizophrenia, pain or sleep disorders. The novel compounds of formula I have good activity and pharmacological properties.

The present invention provides novel compounds of formula I that are inactive at the GABA A receptor complexes, in particular the GABA A α5 receptor.

FIELD OF THE INVENTION

The present invention provides 1,3-dihydro-1,4-benzodiazepine-2-thione compounds that are muscarinic M1 receptor positive allosteric modulators (PAM) and useful in the treatment of diseases, mediated by the muscarinic M1 receptor, such as Alzheimer's disease, cognitive impairment, schizophrenia, pain or sleep disorders, their manufacture, pharmaceutical compositions containing them and their use as therapeutically active substances.

SUMMARY OF THE INVENTION

The present invention provides a compound of formula I,

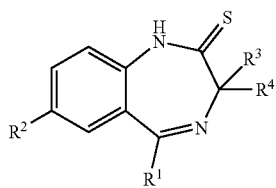

I wherein the substituents and variables are as described below and in the claims, or a pharmaceutically acceptable salt thereof.

The present compounds are muscarinic M1 receptor positive allosteric modulators (PAM) and useful in the treatment of diseases, mediated by the muscarinic M1 receptor, such as Alzheimer's disease, cognitive impairment, schizophrenia, pain or sleep disorders.

DETAILED DESCRIPTION OF THE INVENTION

The present invention provides a compound of formula I and their pharmaceutically acceptable salts thereof, the preparation of the above mentioned compounds, medicaments containing them and their manufacture as well as the use of the above mentioned compounds in the therapeutic and/or prophylactic treatment of Alzheimer's disease, cognitive impairment, schizophrenia, pain or sleep disorders.

The following definitions of the general terms used in the present description apply irrespectively of whether the terms in question appear alone or in combination with other groups.

Unless otherwise stated, the following terms used in this Application, including the specification and claims, have the definitions given below. It must be noted that, as used in the specification and the appended claims, the singular forms "a", "an," and "the" include plural referents unless the context clearly dictates otherwise.

The term "$C_{1-6}$-alkyl", alone or in combination with other groups, stands for a hydrocarbon radical which may be linear or branched, with single or multiple branching, wherein the alkyl group in general comprises 1 to 6 carbon atoms, for example, methyl (Me), ethyl (Et), propyl, isopropyl (i-propyl), n-butyl, i-butyl (isobutyl), 2-butyl (sec-butyl), t-butyl (tert-butyl), isopentyl, 2-ethyl-propyl (2-methyl-propyl), 1,2-dimethyl-propyl and the like. Particular "$C_{1-6}$-alkyl" are "$C_{1-4}$-alkyl". Specific groups are methyl, ethyl, propyl, propoyl, isopropyl and isobutyl.

The term "halogen-$C_{1-6}$-alkyl", alone or in combination with other groups, refers to $C_{1-6}$-alkyl as defined herein, which is substituted by one or multiple halogen, particularly 1-5 halogen, more particularly 1-3 halogen. Particular halogen is fluoro. Particular "halogen-$C_{1-6}$-alkyl" is fluoro-$C_{1-6}$-alkyl and a particular "halogen-$C_{1-3}$-alkyl" is fluoro-$C_{1-3}$-alkyl. Examples are trifluoromethyl, difluoromethyl, fluoromethyl and the like. A specific group is $CF_3$.

The term "$C_{1-6}$-alkoxy-$C_{1-6}$-alkyl", alone or in combination with other groups, refers to $C_{1-6}$-alkyl as defined herein, which is substituted by one or multiple Cis-alkoxy, as defined herein, particularly 1 $C_{1-6}$-alkoxy. A specific group is 1-methoxyethyl.

The term "hydroxy-$C_{1-6}$-alkyl", alone or in combination with other groups, refers to $C_{1-6}$-alkyl as defined herein, which is substituted by one or multiple OH, particularly 1 OH. A specific group is $C(CH_3)_2OH$.

The term "cyano", alone or in combination with other groups, refers to $N\equiv C-$ (NC—).

The term "amino", alone or in combination with other groups, refers to $NH_2$.

The term "nitro", alone or in combination with other groups, refers to $NO_2$.

The term "halogen", alone or in combination with other groups, denotes chloro (Cl), iodo (I), fluoro (F) and bromo (Br). Specific groups are F, Cl and Br.

The term "heteroaryl", alone or in combination with other groups, refers to an aromatic carbocyclic group of having a single 4 to 8 membered ring, in particular 5 to 8, or multiple condensed rings comprising 6 to 14, in particular 6 to 10 ring atoms and containing 1, 2 or 3 heteroatoms individually selected from N, O and S, in particular 1N or 2N, in which group at least one heterocyclic ring is aromatic. Examples of "heteroaryl" include benzofuryl, benzoimidazolyl, 1H-benzoimidazolyl, benzoxazinyl, benzoxazolyl, benzothiazinyl, benzothiazolyl, benzothienyl, benzotriazolyl, furyl, imidazolyl, indazolyl, 1H-indazolyl, indolyl, isoquinolinyl, isothiazolyl, isoxazolyl, oxazolyl, pyrazinyl, pyrazolyl (pyrazyl), 1H-pyrazolyl, pyrazolo[1,5-a]pyridinyl, pyridazinyl, pyridinyl, pyrimidinyl, pyrrolyl, quinolinyl, tetrazolyl, thiazolyl, thienyl, triazolyl, 6,7-dihydro-5H-[1]pyrindinyl and the like. A specific group is pyridinyl.

The term "$C_{1-6}$-alkoxy", alone or in combination with other groups, stands for an —O—$C_{1-6}$-alkyl radical which may be linear or branched, with single or multiple branching, wherein the alkyl group in general comprises 1 to 6 carbon atoms, for example, methoxy (OMe, MeO), ethoxy (OEt), propoxy, isopropoxy (i-propoxy), n-butoxy, i-butoxy (iso-butoxy), 2-butoxy (sec-butoxy), t-butoxy (tert-butoxy), isopentyloxy (i-pentyloxy) and the like. Particular "$C_{1-6}$-alkoxy" are groups with 1 to 4 carbon atoms. Specific is methoxy.

The term "halogen-$C_{1-6}$-alkoxy", alone or in combination with other groups, refers to $C_{1-6}$-alkoxy as defined herein, which is substituted by one or multiple halogen, particularly 1-5 halogen, more particularly 1-3 halogen. Particular halogen is fluoro. Particular "halogen-$C_{1-6}$-alkoxy" is fluoro-$C_{1-6}$-alkoxy and a particular "halogen-$C_{1-3}$-alkoxy" is fluoro-$C_{1-3}$-alkoxy. A specific group is —O—$CF_3$.

The term "aryl" denotes a monovalent aromatic carbocyclic mono- or bicyclic ring system comprising 6 to 10 carbon ring atoms. Examples of aryl moieties include phenyl and benzyl.

The term "$C_{3-7}$-cycloalkyl", alone or in combination with other groups, denotes a monovalent saturated monocyclic or bicyclic hydrocarbon group of 3 to 7 ring carbon atoms, particularly a monovalent saturated monocyclic hydrocarbon group of 3 to 5 ring carbon atoms. Bicyclic means consisting of two saturated carbocycles having one or more carbon atoms in common. Particular cycloalkyl groups are monocyclic. Examples for monocyclic cycloalkyl are cyclopropyl, cyclobutanyl, cyclopentyl, cyclohexyl or cycloheptyl. A specific group is cyclopropyl.

The term "pharmaceutically acceptable salts" refers to salts that are suitable for use in contact with the tissues of humans and animals. Examples of suitable salts with inorganic and organic acids are, but are not limited to acetic acid, citric acid, formic acid, fumaric acid, hydrochloric acid, lactic acid, maleic acid, malic acid, methane-sulfonic acid, nitric acid, phosphoric acid, p-toluenesulphonic acid, succinic acid, sulfuric acid (sulphuric acid), tartaric acid, trifluoroacetic acid and the like. Particular acids are formic acid, trifluoroacetic acid and hydrochloric acid. Specific acids are hydrochloric acid, trifluoroacetic acid and fumaric acid.

The term "ortho-chloro" refers to a chloro substituent in ortho position, in particular in ortho position at a benzene ring.

The terms "pharmaceutically acceptable carrier" and "pharmaceutically acceptable auxiliary substance" refer to carriers and auxiliary substances such as diluents or excipients that are compatible with the other ingredients of the formulation.

The term "pharmaceutical composition" encompasses a product comprising specified ingredients in pre-determined amounts or proportions, as well as any product that results, directly or indirectly, from combining specified ingredients in specified amounts. Particularly it encompasses a product comprising one or more active ingredients, and an optional carrier comprising inert ingredients, as well as any product that results, directly or indirectly, from combination, complexation or aggregation of any two or more of the ingredients, or from dissociation of one or more of the ingredients, or from other types of reactions or interactions of one or more of the ingredients.

The term "inhibitor" denotes a compound which competes with, reduces or prevents the binding of a particular ligand to particular receptor or which reduces or prevents the inhibition of the function of a particular protein.

The term "half maximal effective concentration" (EC50) denotes the plasma concentration of a particular compound required for obtaining 50% of the maximum of a particular effect in vivo.

"Therapeutically effective amount" means an amount of a compound that, when administered to a subject for treating a disease state, is sufficient to effect such treatment for the disease state. The "therapeutically effective amount" will vary depending on the compound, disease state being treated, the severity or the disease treated, the age and relative health of the subject, the route and form of administration, the judgment of the attending medical or veterinary practitioner, and other factors.

The term "as defined herein" and "as described herein" when referring to a variable incorporates by reference the broad definition of the variable as well as particularly, more particularly and most particularly definitions, if any.

The terms "treating", "contacting" and "reacting" when referring to a chemical reaction means adding or mixing two or more reagents under appropriate conditions to produce the indicated and/or the desired product. It should be appreciated that the reaction which produces the indicated and/or the desired product may not necessarily result directly from the combination of two reagents which were initially added, i.e., there may be one or more intermediates which are produced in the mixture which ultimately leads to the formation of the indicated and/or the desired product.

The term "aromatic" denotes the conventional idea of aromaticity as defined in the literature, in particular in IUPAC—Compendium of Chemical Terminology, 2nd, A. D. McNaught & A. Wilkinson (Eds). Blackwell Scientific Publications, Oxford (1997).

The term "pharmaceutically acceptable excipient" denotes any ingredient having no therapeutic activity and being non-toxic such as disintegrators, binders, fillers, solvents, buffers, tonicity agents, stabilizers, antioxidants, surfactants or lubricants used in formulating pharmaceutical products.

Whenever a chiral carbon is present in a chemical structure, it is intended that all stereoisomers associated with that chiral carbon are encompassed by the structure as pure stereoisomers as well as mixtures thereof.

The invention also provides pharmaceutical compositions, methods of using, and methods of preparing the aforementioned compounds.

All separate embodiments may be combined.

One embodiment of the invention provides a compound of formula I,

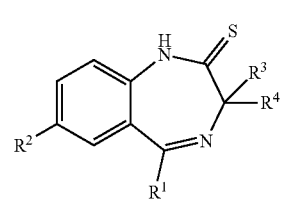

I wherein
$R^1$ is selected from the group consisting of
i) aryl, optionally substituted with $R^5$,
ii) heteroaryl, optionally substituted with $R^5$,
iii) $C_{3-7}$-cycloalkyl, optionally substituted with $R^5$, and
iv) $C_{1-6}$-alkyl;

R² is hydrogen or selected from the group consisting of
  i) $C_{1-6}$-alkyl;
  ii) $C_{1-6}$-alkoxy,
  iii) halogen
  iv) halogen-$C_{1-6}$-alkyl,
  v) halogen-$C_{1-6}$-alkoxy,
  vi) nitro,
  vii) amino, and
  viii) aryl;
R³ is hydrogen or selected from the group consisting of
  i) $C_{1-6}$-alkyl;
  ii) halogen-$C_{1-6}$-alkyl;
  iii) hydroxy-$C_{1-6}$-alkyl,
  iv) $C_{1-6}$-alkoxy-$C_{1-6}$-alkyl,
  v) —(CH₂)$_{1-2}$—S—$C_{1-6}$-alkyl;
  vi) —(CH₂)$_{0-1}$—$C_{3-7}$-cycloalkyl,
  vii) —O—(C=O)—$C_{1-6}$-alkyl, and
  viii) aryl, optionally substituted with 1-2 R⁵;
R⁴ is selected from the group consisting of
  i) hydrogen, and
  ii) $C_{1-6}$-alkyl;
R⁵ is halogen,
with the proviso that R⁵ is not ortho-chloro when R¹ is aryl,
or pharmaceutically acceptable salts thereof;
for the use as therapeutically active substance for the therapeutic and/or prophylactic treatment of Alzheimer's disease, cognitive impairment, schizophrenia, pain or sleep disorders.

A specific embodiment relates to a compound of formula I as described herein that is inactive at the GABA A receptor complexes, in particular the GABA A α5 receptor.

A specific embodiment relates to a compound of formula I as described herein for the use as therapeutically active substance for the therapeutic and/or prophylactic treatment of Alzheimer's disease, cognitive impairment, schizophrenia, pain or sleep disorders, wherein R¹ is phenyl.

A specific embodiment relates to a compound of formula I as described herein for the use as therapeutically active substance for the therapeutic and/or prophylactic treatment of Alzheimer's disease, cognitive impairment, schizophrenia, pain or sleep disorders, wherein R² is halogen, in particular Cl.

A specific embodiment relates to a compound of formula I as described herein for the use as therapeutically active substance for the therapeutic and/or prophylactic treatment of Alzheimer's disease, cognitive impairment, schizophrenia, pain or sleep disorders, that is selected from the group consisting of
(3R)-3-benzyl-7-chloro-5-phenyl-1,3-dihydro-1,4-benzodiazepine-2-thione,
(3R)-7-chloro-3-(2-methylsulfanylethyl)-5-phenyl-1,3-dihydro-1,4-benzodiazepine-2-thione,
(3R)-7-chloro-3-isopropyl-5-phenyl-1,3-dihydro-1,4-benzodiazepine-2-thione,
(3R)-7-chloro-5-(2-fluorophenyl)-3-(trifluoromethyl)-1,3-dihydro-1,4-benzodiazepine-2-thione,
(3R)-7-chloro-5-(2-fluorophenyl)-3-isopropyl-1,3-dihydro-1,4-benzodiazepine-2-thione,
(3S)-3-benzyl-7-chloro-5-phenyl-1,3-dihydro-1,4-benzodiazepine-2-thione,
(3S)-3-isopropyl-5,7-diphenyl-1,3-dihydro-1,4-benzodiazepine-2-thione,
(3S)-3-isopropyl-5-phenyl-7-(trifluoromethoxy)-1,3-dihydro-1,4-benzodiazepine-2-thione,
(3S)-3-isopropyl-5-phenyl-7-(trifluoromethyl)-1,3-dihydro-1,4-benzodiazepine-2-thione,
(3S)-3-isopropyl-7-methoxy-5-phenyl-1,3-dihydro-1,4-benzodiazepine-2-thione,
(3S)-5-(2-fluorophenyl)-3-isopropyl-7-methyl-1,3-dihydro-1,4-benzodiazepine-2-thione,
(3S)-7-bromo-3-isopropyl-5-(2-pyridyl)-1,3-dihydro-1,4-benzodiazepine-2-thione,
(3S)-7-bromo-3-isopropyl-5-(3-pyridyl)-1,3-dihydro-1,4-benzodiazepine-2-thione,
(3S)-7-chloro-3-(2-methylsulfanylethyl)-5-phenyl-1,3-dihydro-1,4-benzodiazepine-2-thione,
(3S)-7-chloro-3-(cyclopropylmethyl)-5-phenyl-1,3-dihydro-1,4-benzodiazepine-2-thione,
(3S)-7-chloro-3-cyclopropyl-5-phenyl-1,3-dihydro-1,4-benzodiazepine-2-thione,
(3S)-7-chloro-3-ethyl-5-phenyl-1,3-dihydro-1,4-benzodiazepine-2-thione,
(3S)-7-chloro-3-isobutyl-5-phenyl-1,3-dihydro-1,4-benzodiazepine-2-thione,
(3S)-7-chloro-3-isopropyl-5-phenyl-1,3-dihydro-1,4-benzodiazepine-2-thione,
(3S)-7-chloro-3-methyl-5-phenyl-3-propyl-1H-1,4-benzodiazepine-2-thione,
(3S)-7-chloro-5-(2-fluorophenyl)-3-(trifluoromethyl)-1,3-dihydro-1,4-benzodiazepine-2-thione,
(3S)-7-chloro-5-(2-fluorophenyl)-3-isobutyl-1,3-dihydro-1,4-benzodiazepine-2-thione,
(3S)-7-chloro-5-(2-fluorophenyl)-3-isopropyl-1,3-dihydro-1,4-benzodiazepine-2-thione,
(3S)-7-chloro-5-(2-fluorophenyl)-3-phenyl-1,3-dihydro-1,4-benzodiazepine-2-thione,
(3S)-7-chloro-5-(3-chlorophenyl)-3-isopropyl-1,3-dihydro-1,4-benzodiazepine-2-thione,
(3S)-7-chloro-5-cyclohexyl-3-isopropyl-1,3-dihydro-1,4-benzodiazepine-2-thione,
(3S)-7-chloro-5-phenyl-3-(2,2,2-trifluoroethyl)-1,3-dihydro-1,4-benzodiazepine-2-thione,
(3S)-7-chloro-5-phenyl-3-propyl-1,3-dihydro-1,4-benzodiazepine-2-thione,
(3S)-8-chloro-5-(2-fluorophenyl)-3-isopropyl-1,3-dihydro-1,4-benzodiazepine-2-thione,
[7-chloro-5-(2-fluorophenyl)-2-thioxo-1,3-dihydro-1-benzazepin-3-yl]acetate,
(3S)-5-(4-fluorophenyl)-3-isopropyl-7-(trifluoromethoxy)-1,3-dihydro-1,4-benzodiazepine-2-thione,
3-[(3,4-dichlorophenyl)methyl]-5-phenyl-1,3-dihydro-1,4-benzodiazepine-2-thione,
3-methyl-5-phenyl-1,3-dihydro-1,4-benzodiazepine-2-thione,
3-methyl-7-nitro-5-phenyl-1,3-dihydro-1,4-benzodiazepine-2-thione,
5-cyclohexyl-7-(trifluoromethyl)-1,3-dihydro-1,4-benzodiazepine-2-thione,
7-amino-3-ethyl-5-(2-fluorophenyl)-1,3-dihydro-1,4-benzodiazepine-2-thione,
7-chloro-3-(1-hydroxy-1-methyl-ethyl)-5-phenyl-1,3-dihydro-1,4-benzodiazepine-2-thione,
7-chloro-3-(1-methoxyethyl)-5-phenyl-1,3-dihydro-1,4-benzodiazepine-2-thione,
7-chloro-3,5-diphenyl-1,3-dihydro-1,4-benzodiazepine-2-thione,
7-chloro-3-isopropyl-5-phenyl-1,3-dihydro-1,4-benzodiazepine-2-thione, and
7-chloro-5-propyl-1,3-dihydro-1,4-benzodiazepine-2-thione,
or pharmaceutically acceptable salts thereof.

A specific embodiment relates to a compound of formula I as described herein

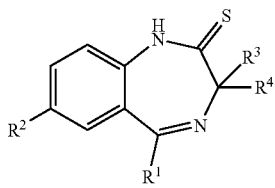

wherein
$R^1$ is selected from the group consisting of
  i) aryl, optionally substituted with $R^5$,
  ii) heteroaryl, optionally substituted with $R^5$,
  iii) $C_{3-7}$-cycloalkyl, optionally substituted with $R^5$, and
  iv) $C_{1-6}$-alkyl;
$R^2$ is hydrogen or selected from the group consisting of
  i) $C_{1-6}$-alkyl,
  ii) $C_{1-6}$-alkoxy,
  iii) halogen
  iv) halogen-$C_{1-6}$-alkyl,
  v) halogen-$C_{1-6}$-alkoxy,
  vi) nitro,
  vii) amino, and
  viii) aryl;
$R^3$ is hydrogen or selected from the group consisting of
  i) halogen-$C_{1-6}$-alkyl,
  ii) hydroxy-$C_{1-6}$-alkyl,
  iii) $C_{1-6}$-alkoxy-$C_{1-6}$-alkyl,
  iv) —$(CH_2)_{1-2}$—S—$C_{1-6}$-alkyl,
  v) —$(CH_2)_{0-1}$—$C_{3-7}$-cycloalkyl,
  vi) —O—(C=O)—$C_{1-6}$-alkyl, and
  vii) aryl, optionally substituted with 1-2 $R^5$;
$R^4$ is selected from the group consisting of
  i) hydrogen, and
  ii) $C_{1-6}$-alkyl;
$R^5$ is halogen;
with the proviso that $R^5$ is not ortho-chloro when $R^1$ is aryl,
or pharmaceutically acceptable salts thereof.

A specific embodiment relates to a compound of formula I as described herein

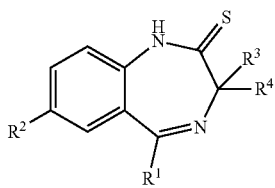

wherein
$R^1$ is selected from the group consisting of
  i) aryl, optionally substituted with $R^5$,
  ii) heteroaryl, optionally substituted with $R^5$,
  iii) $C_{3-7}$-cycloalkyl, optionally substituted with $R^5$, and
  iv) $C_{1-6}$-alkyl;
$R^2$ is hydrogen or selected from the group consisting of
  i) $C_{1-6}$-alkyl,
  ii) $C_{1-6}$-alkoxy,
  iii) halogen
  iv) halogen-$C_{1-6}$-alkyl,
  v) halogen-$C_{1-6}$-alkoxy,
  vi) nitro,
  vii) amino, and
  viii) aryl;
$R^3$ is hydrogen or selected from the group consisting of
  i) $C_{1-6}$-alkyl,
  ii) halogen-$C_{1-6}$-alkyl,
  iii) hydroxy-$C_{1-6}$-alkyl,
  iv) $C_{1-6}$-alkoxy-$C_{1-6}$-alkyl,
  v) —$(CH_2)_{1-2}$—S—$C_{1-6}$-alkyl,
  vi) —$(CH_2)_{0-1}$—$C_{3-7}$-cycloalkyl,
  vii) —O—(C=O)—$C_{1-6}$-alkyl, and
  viii) aryl, optionally substituted with 1-2 $R^5$;
$R^4$ is selected from the group consisting of
  i) hydrogen, and
  ii) $C_{1-6}$-alkyl;
$R^5$ is halogen;
with the proviso that $R^5$ is not ortho-chloro when $R^1$ is aryl,
and that the following compounds are excluded:
7-chloro-3-methyl-5-phenyl-1,3-dihydro-1,4-benzodiazepine-2-thione,
7-chloro-5-(2-fluorophenyl)-3-ethyl-1,3-dihydro-1,4-benzodiazepine-2-thione,
7-chloro-5-phenyl-3-ethyl-1,3-dihydro-1,4-benzodiazepine-2-thione,
5-(2-fluorophenyl)-3-ethyl-1,3-dihydro-1,4-benzodiazepine-2-thione,
5-phenyl-3-ethyl-1,3-dihydro-1,4-benzodiazepine-2-thione
3-isobutyl-5-phenyl-1,3-dihydro-1,4-benzodiazepine-2-thione,
7-bromo-3-methyl-5-(2-pyridyl)-1,3-dihydro-1,4-benzodiazepine-2-thione,
3-methyl-5-(2-pyridyl)-1,3-dihydro-1,4-benzodiazepine-2-thione,
7-chloro-3-methyl-5-(2-pyridyl)-1,3-dihydro-1,4-benzodiazepine-2-thione, and
7-trifluoromethyl-3-methyl-5-(2-pyridyl)-1,3-dihydro-1,4-benzodiazepine-2-thione.
or pharmaceutically acceptable salts thereof.

A specific embodiment relates to a compound of formula I as described herein, wherein $R^1$ is selected from the group consisting of benzyl, cyclohexyl, ethyl, phenyl and pyridyl.

A specific embodiment relates to a compound of formula I as described herein, wherein $R^1$ is aryl, in particular phenyl.

A specific embodiment relates to a compound of formula I as described herein, wherein $R^2$ is selected from the group consisting of amino, Br, $CF_3$, Cl, methyl, $NO_2$, $OCF_3$, $OCH_3$ and phenyl.

A specific embodiment relates to a compound of formula I as described herein, wherein $R^2$ is halogen, in particular Cl.

A specific embodiment relates to a compound of formula I as described herein, wherein $R^3$ is selected from the group consisting of
  i) $C_{1-6}$-alkyl,
  ii) halogen-$C_{1-6}$-alkyl,
  iii) hydroxy-$C_{1-6}$-alkyl,
  iv) $C_{1-6}$-alkoxy-$C_{1-6}$-alkyl,
  v) —$(CH_2)_{12}$—S—$C_{1-6}$-alkyl,
  vi) —$(CH_2)_{0-1}$—$C_{3-7}$-cycloalkyl,
  vii) —O—(C=O)—$C_{1-6}$-alkyl, and
  viii) aryl, optionally substituted with 1-2 halogen, in particular F.

A specific embodiment relates to a compound of formula I as described herein, wherein $R^3$ is selected from the group consisting of —$(CH_2)_2$—S—$CH_3$, 1-methoxyethyl, 3,4-dichlorobenzyl, benzyl, $C((CH_3)_2, OH)$, $CF_3$, $CH_2CF_3$, $CH_2$-cyclopropyl, cyclopropyl, ethyl, isobutyl, isopropyl, methyl, —O—C(O)—$CH_3$, phenyl and propyl.

A specific embodiment relates to a compound of formula I as described herein, wherein $R^3$ is $C_{1-6}$-alkyl, in particular isopropyl.

A specific embodiment relates to a compound of formula I as described herein, wherein $R^4$ is H.

A specific embodiment relates to a compound of formula I as described herein, wherein $R^1$ is aryl.

A specific embodiment relates to a compound of formula I as described herein, wherein $R^1$ is phenyl.

A specific embodiment relates to a compound of formula I as described herein, wherein $R^2$ is hydrogen or halogen.

A specific embodiment relates to a compound of formula I as described herein, wherein $R^2$ is hydrogen.

A specific embodiment relates to a compound of formula I as described herein, wherein $R^2$ is Cl.

A specific embodiment relates to a compound of formula I as described herein, wherein $R^3$ is $C_{1-6}$-alkyl.

A specific embodiment relates to a compound of formula I as described herein, wherein $R^3$ is isopropyl.

A certain embodiment of the invention provides a compound of formula I as described herein, whenever prepared by a process as defined herein.

A certain embodiment of the invention provides a compound of formula I as described herein for use as therapeutically active substance.

A certain embodiment of the invention provides a compound of formula I as described herein for the use as muscarinic M1 receptor positive allosteric modulator.

A certain embodiment of the invention provides a compound of formula I as described herein for the use as therapeutically active substance for the therapeutic and/or prophylactic treatment of Alzheimer's disease, cognitive impairment, schizophrenia, pain or sleep disorders.

A certain embodiment of the invention provides a compound of formula I as described herein for the use as therapeutically active substance for the treatment of Alzheimer's disease, cognitive impairment, schizophrenia, pain or sleep disorders.

A certain embodiment of the invention provides a pharmaceutical composition comprising a compound of formula I as described herein and a pharmaceutically acceptable carrier and/or a pharmaceutically acceptable auxiliary substance.

A certain embodiment of the invention provides the use of a compound of formula I as described herein for the manufacture of a medicament for the use as muscarinic M1 receptor positive allosteric modulator.

A certain embodiment of the invention provides the use of a compound of formula I as described herein for the manufacture of a medicament for the therapeutically active substance for the therapeutic and/or prophylactic treatment of Alzheimer's disease, cognitive impairment, schizophrenia, pain or sleep disorders.

A certain embodiment of the invention provides a method for the use as muscarinic M1 receptor positive allosteric modulator, particularly for the therapeutically active substance for the therapeutic and/or prophylactic treatment of Alzheimer's disease, cognitive impairment, schizophrenia, pain or sleep disorders.

Furthermore, the invention includes all optical isomers, i.e. diastereoisomers, diastereomeric mixtures, racemic mixtures, all their corresponding enantiomers and/or tautomers as well as their solvates of the compounds of formula I.

The compounds of formula I may contain one or more asymmetric centers and can therefore occur as racemates, racemic mixtures, single enantiomers, diastereomeric mixtures and individual diastereomers. Additional asymmetric centers may be present depending upon the nature of the various substituents on the molecule. Each such asymmetric center will independently produce two optical isomers and it is intended that all of the possible optical isomers and diastereomers in mixtures and as pure or partially purified compounds are included within this invention. The present invention is meant to encompass all such isomeric forms of these compounds. The independent syntheses of these diastereomers or their chromatographic separations may be achieved as known in the art by appropriate modification of the methodology disclosed herein. Their absolute stereochemistry may be determined by the x-ray crystallography of crystalline products or crystalline intermediates which are derivatized, if necessary, with a reagent containing an asymmetric center of known absolute configuration. If desired, racemic mixtures of the compounds may be separated so that the individual enantiomers are isolated. The separation can be carried out by methods well known in the art, such as the coupling of a racemic mixture of compounds to an enantiomerically pure compound to form a diastereomeric mixture, followed by separation of the individual diastereomers by standard methods, such as fractional crystallization or chromatography.

In the embodiments, where optically pure enantiomers are provided, optically pure enantiomer means that the compound contains >90% of the desired isomer by weight, particularly >95% of the desired isomer by weight, or more particularly >99% of the desired isomer by weight, said weight percent based upon the total weight of the isomer(s) of the compound. Chirally pure or chirally enriched compounds may be prepared by chirally selective synthesis or by separation of enantiomers. The separation of enantiomers may be carried out on the final product or alternatively on a suitable intermediate.

The compounds of formula I may be prepared in accordance with the schemes described in the examples. The starting material is commercially available or may be prepared in accordance with known methods.

The corresponding pharmaceutically acceptable salts with acids can be obtained by standard methods known to the person skilled in the art, e.g. by dissolving the compound of formula I in a suitable solvent such as e.g. dioxane or tetrahydrofuran and adding an appropriate amount of the corresponding acid. The products can usually be isolated by filtration or by chromatography. The conversion of a compound of formula I into a pharmaceutically acceptable salt with a base can be carried out by treatment of such a compound with such a base. One possible method to form such a salt is e.g. by addition of 1/n equivalents of a basic salt such as e.g. $M(OH)_n$, wherein M=metal or ammonium cation and n=number of hydroxide anions, to a solution of the compound in a suitable solvent (e.g. ethanol, ethanol-water mixture, tetrahydrofuran-water mixture) and to remove the solvent by evaporation or lyophilisation. Particular salts are hydrochloride, formate and trifluoroacetate.

Insofar as their preparation is not described in the examples, the compounds of formula I as well as all intermediate products can be prepared according to analogous methods or according to the methods set forth herein. Starting materials are commercially available, known in the art or can be prepared by methods known in the art or in analogy thereto.

It will be appreciated that the compounds of general formula I in this invention may be derivatised at functional groups to provide derivatives which are capable of conversion back to the parent compound in vivo.

Pharmacological Tests

The compounds of formula I and their pharmaceutically acceptable salts possess valuable pharmacological properties. It has been found that the compounds of the present invention are associated with modulation of the muscarinic M1 receptor. The compounds were investigated in accordance with the test given hereinafter.

The assay is designed to select compounds that possess modulator activity at the acetylcholine muscarinic receptor expressed in CHO cells by measuring the intracellular calcium with a Fluorometric Imaging Plate Reader System (FLIPR, Molecular Devices). The assay study the effect of several concentrations of test compounds on basal or acetylcholine-stimulated $Ca^{2+}$ levels using FLIPR.

CHO human M1 are plated the day before the experiments at $2\times10^5$ cells/ml in PDL BioCoat 96 well black/clear plate (Becton 35 4640). The cells are grown at 37° C. and 5% $CO_2$ in the following medium: F12 Nut Mix (Gibco 21765), 10% FCS heat inactivated (GIBCO 16000-044), 1% Pen Strep (Gibco, 15140) and 200 μg/ml Geneticin (Gibco 11811). On the day of the experiment, the medium was removed and replaced by 100 μl of dye loading buffer containing Hanks Balanced Salt solution (HBSS, 14065-049, Gibco) with 20 mM HEPES (Gibco 15630-056), 2 mM Probenicid (Sigma P8761), 2 mM Fluo-4AM ester (Molecular Probes F-14202), 10% Pluronic acid Molecular Probes P-3000) pH=7.4 and incubated at 37° C. After 60 minutes extracellular dye was removed and the cells were washed five times with FLIPR buffer containing HBSS (Gibco 14065-049) with 20 mM HEPES (Gibco, 15630-056), 2 mM Probenicid (Sigma P8761) pre-warmed at 37° C. using and Ebml cell washer leaving 100 μl of FLIPR buffer in each well. The cell plate and the diluted compounds (1% DMSO final concentration) are placed on the platform of the FLIPR and the door closed. A signal test to check background fluorescence and basal fluorescence signal is performed. Laser intensity is adjusted if necessary. Two minutes preincubation with the diluted test compounds is provide to determine any agonist activity on the M1 receptor by comparison to 30 nM Acetylcholine control. In order to determine any modulator activity the diluted compounds were added to cells and after two minutes preincubation, the EC20 of acetylcholine is added followed by another two minutes preincubation before the measurement of intracellular $Ca^{2+}$ with a FLIPR (Molecular Devices).

Table 1

| Exam. | Structure | $IC_{50}$ value hM1 [nM] |
|---|---|---|
| 1 | Chiral | 312 |
| 2 | Chiral | 289 |
| 3 | Chiral | 311 |
| 4 | Chiral | 103 |
| 5 | Chiral | 80 |
| 6 | Chiral | 104 |

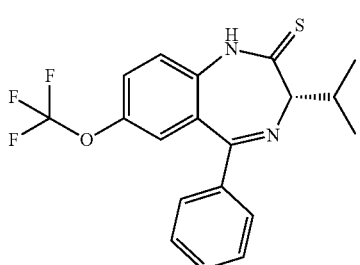

Table 1-continued

| Exam. | Structure | IC$_{50}$ value hM1 [nM] |
|---|---|---|
| 7 | Chiral; 7-chloro-5-phenyl-3-propyl-1,3-dihydro-2H-benzo[e][1,4]diazepine-2-thione | 187 |
| 8 | Chiral; 7-chloro-5-phenyl-3-(2,2,2-trifluoroethyl)-1,3-dihydro-2H-benzo[e][1,4]diazepine-2-thione | 238 |
| 9 | Chiral; 7-chloro-3-(2-(methylthio)ethyl)-5-phenyl-1,3-dihydro-2H-benzo[e][1,4]diazepine-2-thione | 504 |
| 10 | Chiral; 7-chloro-5-(2-fluorophenyl)-3-(trifluoromethyl)-1,3-dihydro-2H-benzo[e][1,4]diazepine-2-thione | 610 |
| 11 | Chiral; 7-chloro-5-(2-fluorophenyl)-3-(trifluoromethyl)-1,3-dihydro-2H-benzo[e][1,4]diazepine-2-thione | 622 |
| 12 | 3-methyl-8-nitro-5-phenyl-3,4-dihydro-1H-benzo[e][1,4]diazepine-2-thione | 732 |
| 13 | Chiral; 5-(2-fluorophenyl)-3-isopropyl-7-methyl-1,3-dihydro-2H-benzo[e][1,4]diazepine-2-thione | 62 |
| 14 | 8-chloro-6-(2-fluorophenyl)-2-thioxo-2,3-dihydro-1H-benzo[b]azepin-3-yl acetate | 649 |
| 15 | 7-chloro-3-isopropyl-5-phenyl-1,3-dihydro-2H-benzo[e][1,4]diazepine-2-thione | 64 |
| 16 | Chiral; 7-chloro-3-isopropyl-5-phenyl-1,3-dihydro-2H-benzo[e][1,4]diazepine-2-thione | 70 |

TABLE 1-continued

| Exam. | Structure | IC₅₀ value hM1 [nM] |
|---|---|---|
| 17 | 5-propyl-7-chloro-1,3-dihydro-2H-1,4-benzodiazepine-2-thione | 1'277 |
| 18 | Chiral; 3-isopropyl-7-trifluoromethyl-5-phenyl-1,3-dihydro-2H-1,4-benzodiazepine-2-thione | 71 |
| 19 | Chiral; 3-isopropyl-7-phenyl-5-phenyl-1,3-dihydro-2H-1,4-benzodiazepine-2-thione | 1'469 |
| 20 | 5-cyclohexyl-7-trifluoromethyl-1,3-dihydro-2H-1,4-benzodiazepine-2-thione | 1'955 |
| 21 | Chiral; 3-benzyl-5-phenyl-7-chloro-1,3-dihydro-2H-1,4-benzodiazepine-2-thione | 1'144 |
| 22 | Chiral; 3-isopropyl-7-chloro-5-(3-chlorophenyl)-1,3-dihydro-2H-1,4-benzodiazepine-2-thione | 172 |
| 23 | Chiral; 3-isopropyl-8-chloro-5-(2-fluorophenyl)-1,3-dihydro-2H-1,4-benzodiazepine-2-thione | 399 |
| 24 | Chiral; 3-cyclopropyl-7-chloro-5-phenyl-1,3-dihydro-2H-1,4-benzodiazepine-2-thione | 165 |
| 25 | Chiral; 3-isopropyl-7-trifluoromethoxy-5-phenyl-1,3-dihydro-2H-1,4-benzodiazepine-2-thione | 232 |
| 26 | 3-(2-hydroxypropan-2-yl)-7-chloro-5-phenyl-1,3-dihydro-2H-1,4-benzodiazepine-2-thione | 1'846 |

TABLE 1-continued

| Exam. | Structure | IC$_{50}$ value hM1 [nM] |
|---|---|---|
| 27 | Chiral | 641 |
| 28 | 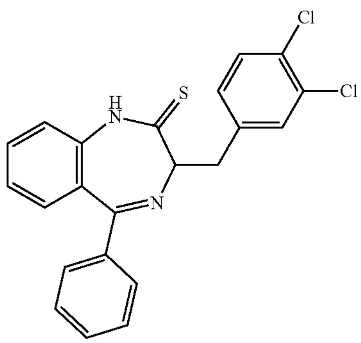 [SMILES: S=C1Nc2ccccc2C(c2ccccc2)=NC1Cc1ccc(Cl)c(Cl)c1] | 1'668 |
| 29 | Chiral | 1'465 |
| 30 | Chiral | 251 |
| 31 | 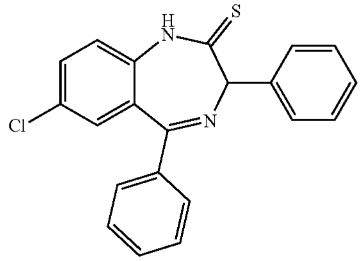 [SMILES: S=C1Nc2ccc(Cl)cc2C(c2ccccc2)=NC1c1ccccc1] | 799 |
| 32 | Chiral | 275 |
| 33 | | 1'205 |
| 34 | Chiral | 420 |
| 35 | Chiral | 521 |
| 36 | Chiral | 317 |

Table 1-continued

| Exam. | Structure | IC$_{50}$ value hM1 [nM] |
|---|---|---|
| 37 | 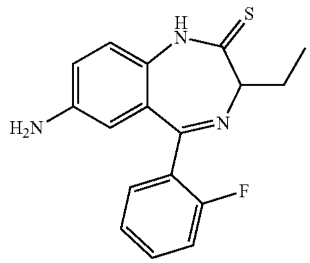 [SMILES: CCC1N=C(c2ccccc2F)c2cc(N)ccc2NC1=S] | 6'058 |
| 38 | 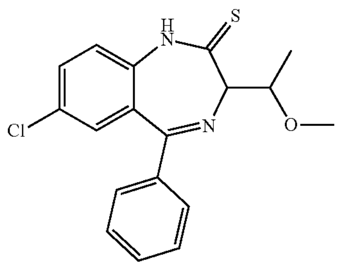 [SMILES: COC(C)C1N=C(c2ccccc2)c2cc(Cl)ccc2NC1=S] | 354 |
| 39 | Chiral | 414 |
| 40 | Chiral | 559 |
| 41 | 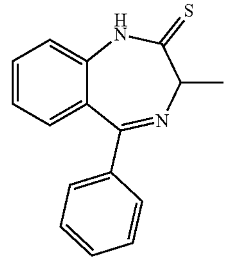 [SMILES: CC1N=C(c2ccccc2)c2ccccc2NC1=S] | 552 |
| 42 | | 50 |

GABA A Assay

The ability of compounds present invention to bind to GABA A receptor subtypes was determined by competition for [$^3$H]flumazenil (85 Ci/mmol; Roche) binding to HEK293 cells expressing human (transiently transfected) receptors of composition α1β2γ2, and α5β3γ2.

Membrane preparation Cell pellets were suspended in Krebs-tris buffer (5 mM KCl, 1.25 mM CaCl$_2$), 1.25 mM MgCl$_2$, 120 mM NaCl, 15 mM Tris; pH 7.5; binding assay buffer), homogenized by polytron for ca. 20 sec on ice and centrifuged for 60 min at 4° C. (50000 g; Sorvall, rotor: SM24=20000 rpm). The cell pellets were resuspended in Krebs-tris buffer and homogenized by polytron for ca. 15 sec on ice. Protein was measured (Bradford method, Bio-Rad) and aliquots of 1 mL were prepared and stored at −80° C.

Radioligand Binding Assay

Radioligand binding assays were carried out in a volume of 200 uL (96-well plates) which contained 100 μL of cell membranes, [3H]flumazenil at a concentration of 1 nM for a1, a2, a3 subunits and 1 nM for a5 subunits and the test compound in the range of 3.16 μM to 0.1 μM. Nonspecific binding was defined by 10$^{-5}$ M diazepam and typically represented less than 5% of the total binding. Assays were incubated to equilibrium for 1 hour at 4° C. and harvested onto GF/C uni-filters (Packard) by filtration using a Packard harvester and washing with ice-cold wash buffer (50 mM Tris; pH 7.5). After drying, filter-retained radioactivity was detected by liquid scintillation counting.

Data Calculation

K$_i$ values were calculated using Excel-Fit (Microsoft) and are the means of two determinations.

Example 5: GABA-A alpha5: Ki>24 μM; GABA-A alpha 5: >36 μM; Oocyte EP no effect at 1 μM.

Pharmaceutical Compositions

The compounds of formula I and the pharmaceutically acceptable salts can be used as therapeutically active substances, e.g. in the form of pharmaceutical preparations. The pharmaceutical preparations can be administered orally, e.g. in the form of tablets, coated tablets, dragées, hard and soft gelatin capsules, solutions, emulsions or suspensions. The administration can, however, also be effected rectally, e.g. in the form of suppositories, or parenterally, e.g. in the form of injection solutions.

The compounds of formula I and the pharmaceutically acceptable salts thereof can be processed with pharmaceutically inert, inorganic or organic carriers for the production of pharmaceutical preparations. Lactose, corn starch or derivatives thereof, talc, stearic acids or its salts and the like can be used, for example, as such carriers for tablets, coated tablets, dragées and hard gelatin capsules. Suitable carriers for soft gelatin capsules are, for example, vegetable oils, waxes, fats, semi-solid and liquid polyols and the like. Depending on the nature of the active substance no carriers are however usually required in the case of soft gelatin capsules. Suitable carriers for the production of solutions and syrups are, for example, water, polyols, glycerol, vegetable oil and the like. Suitable carriers for suppositories are, for example, natural or hardened oils, waxes, fats, semi-liquid or liquid polyols and the like.

The pharmaceutical preparations can, moreover, contain pharmaceutically acceptable auxiliary substances such as preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

Medicaments containing a compound of formula I or a pharmaceutically acceptable salt thereof and a therapeutically inert carrier are also provided by the present invention, as is a process for their production, which comprises bringing one or more compounds of formula I and/or pharmaceutically acceptable salts thereof and, if desired, one or more other therapeutically valuable substances into a galenical administration form together with one or more therapeutically inert carriers.

The dosage can vary within wide limits and will, of course, have to be adjusted to the individual requirements in each particular case. In the case of oral administration the dosage for adults can vary from about 0.01 mg to about 1000 mg per day of a compound of general formula I or of the corresponding amount of a pharmaceutically acceptable salt thereof. The daily dosage may be administered as single dose or in divided doses and, in addition, the upper limit can also be exceeded when this is found to be indicated.

The following examples illustrate the present invention without limiting it, but serve merely as representative thereof. The pharmaceutical preparations conveniently contain about 1-500 mg, particularly 1-100 mg, of a compound of formula I. Examples of compositions according to the invention are:

Example A

Tablets of the following composition are manufactured in the usual manner:

TABLE 2 possible tablet composition

| ingredient | mg/tablet | | | |
|---|---|---|---|---|
| | 5 | 25 | 100 | 500 |
| Compound of formula I | 5 | 25 | 100 | 500 |
| Lactose Anhydrous DTG | 125 | 105 | 30 | 150 |
| Sta-Rx 1500 | 6 | 6 | 6 | 60 |
| Microcrystalline Cellulose | 30 | 30 | 30 | 450 |
| Magnesium Stearate | 1 | 1 | 1 | 1 |
| Total | 167 | 167 | 167 | 831 |

Manufacturing Procedure
1. Mix ingredients 1, 2, 3 and 4 and granulate with purified water.
2. Dry the granules at 50° C.
3. Pass the granules through suitable milling equipment.
4. Add ingredient 5 and mix for three minutes; compress on a suitable press.

Example B-1

Capsules of the following composition are manufactured:

TABLE 3 possible capsule ingredient composition

| ingredient | mg/capsule | | | |
|---|---|---|---|---|
| | 5 | 25 | 100 | 500 |
| Compound of formula I | 5 | 25 | 100 | 500 |
| Hydrous Lactose | 159 | 123 | 148 | — |
| Corn Starch | 25 | 35 | 40 | 70 |
| Talk | 10 | 15 | 10 | 25 |
| Magnesium Stearate | 1 | 2 | 2 | 5 |
| Total | 200 | 200 | 300 | 600 |

Manufacturing Procedure
1. Mix ingredients 1, 2 and 3 in a suitable mixer for 30 minutes.
2. Add ingredients 4 and 5 and mix for 3 minutes.
3. Fill into a suitable capsule.

The compound of formula I, lactose and corn starch are firstly mixed in a mixer and then in a comminuting machine. The mixture is returned to the mixer; the talc is added thereto and mixed thoroughly. The mixture is filled by machine into suitable capsules, e.g. hard gelatin capsules.

Example B-2

Soft Gelatin Capsules of the following composition are manufactured:

TABLE 4 possible soft gelatin capsule ingredient composition

| ingredient | mg/capsule |
|---|---|
| Compound of formula I | 5 |
| Yellow wax | 8 |
| Hydrogenated Soya bean oil | 8 |
| Partially hydrogenated plant oils | 34 |
| Soya bean oil | 110 |
| Total | 165 |

TABLE 5 possible soft gelatin capsule composition

| ingredient | mg/capsule |
|---|---|
| Gelatin | 75 |
| Glycerol 85% | 32 |
| Karion 83 | 8 (dry matter) |
| Titan dioxide | 0.4 |
| Iron oxide yellow | 1.1 |
| Total | 116.5 |

Manufacturing Procedure

The compound of formula I is dissolved in a warm melting of the other ingredients and the mixture is filled into soft gelatin capsules of appropriate size. The filled soft gelatin capsules are treated according to the usual procedures.

Example C

Suppositories of the following composition are manufactured:

TABLE 6

| possible suppository composition | |
| --- | --- |
| ingredient | mg/supp. |
| Compound of formula I | 15 |
| Suppository mass | 1285 |
| Total | 1300 |

Manufacturing Procedure

The suppository mass is melted in a glass or steel vessel, mixed thoroughly and cooled to 45° C. Thereupon, the finely powdered compound of formula I is added thereto and stirred until it has dispersed completely. The mixture is poured into suppository moulds of suitable size, left to cool; the suppositories are then removed from the moulds and packed individually in wax paper or metal foil.

Example D

Injection solutions of the following composition are manufactured:

TABLE 7

| possible injection solution composition | |
| --- | --- |
| ingredient | mg/injection solution. |
| Compound of formula I | 3 |
| Polyethylene Glycol 400 | 150 |
| acetic acid | q.s. ad pH 5.0 |
| water for injection solutions | ad 1.0 ml |

Manufacturing Procedure

The compound of formula I is dissolved in a mixture of Polyethylene Glycol 400 and water for injection (part). The pH is adjusted to 5.0 by acetic acid. The volume is adjusted to 1.0 ml by addition of the residual amount of water. The solution is filtered, filled into vials using an appropriate overage and sterilized.

Example E

Sachets of the following composition are manufactured:

TABLE 8

| possible sachet composition | |
| --- | --- |
| ingredient | mg/sachet |
| Compound of formula I | 50 |
| Lactose, fine powder | 1015 |
| Microcrystalline cellulose (AVICEL PH 102) | 1400 |
| Sodium carboxymethyl cellulose | 14 |
| Polyvinylpyrrolidon K 30 | 10 |
| Magnesium stearate | 10 |
| Flavoring additives | 1 |
| Total | 2500 |

Manufacturing Procedure

The compound of formula I is mixed with lactose, microcrystalline cellulose and sodium carboxymethyl cellulose and granulated with a mixture of polyvinylpyrrolidone in water. The granulate is mixed with magnesium stearate and the flavoring additives and filled into sachets.

EXPERIMENTAL PART

The following examples are provided for illustration of the invention. They should not be considered as limiting the scope of the invention, but merely as being representative thereof.

Example 1

(3S)-5-(4-fluorophenyl)-3-isopropyl-7-(trifluoromethoxy)-1,3-dihydro-1,4-benzodiazepine-2-thione a) {(S)-1-[2-(4-Fluoro-benzoyl)-4-trifluoromethoxy-phenylcarbamoyl]-2-methyl-propyl}-carbamic Acid Tert-Butyl Ester

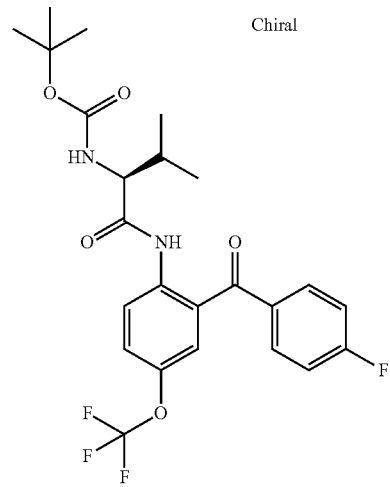 [SMILES: CC(C)[C@H](NC(=O)OC(C)(C)C)C(=O)Nc1ccc(OC(F)(F)F)cc1C(=O)c1ccc(F)cc1]

A mixture of (2-amino-5-(trifluoromethoxy)phenyl)(4-fluorophenyl)methanone (180 mg, 602 μmol, Eq: 1.00), (S)-2-(tert-butoxycarbonylamino)-3-methylbutanoic acid (131 mg, 602 Eq: 1.00) in pyridine (5.4 ml) was stirred at −20° C. under nitrogen atmosphere, then phosphorus oxychloride (101 mg, 61.7 μl, 662 μmol, Eq: 1.1) was added and stirring was continued at this temperature for 50 minutes. The mixture was quenched by the addition of ice water. The mixture was extracted two times with ethyl acetate, the organic layers were combined, washed with sodiumhydrogen carbonate sat. and brine, dried over magnesium sulfate filtrated and evaporated affording {(S)-1-[2-(4-Fluoro-benzoyl)-4-trifluoromethoxy-phenylcarbamoyl]-2-methyl-propyl}-carbamic acid tert-butyl ester (245 mg, 81.7%) as an orange viscous oil. M+H+=497.3 b) (S)-5-(4-Fluoro-phenyl)-3-isopropyl-7-trifluoromethoxy-1,3-dihydro-benzo[e][1,4]diazepin-2-one

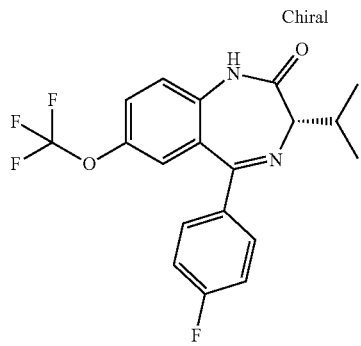 [SMILES: CC(C)[C@@H]1N=C(c2ccc(F)cc2)c2cc(OC(F)(F)F)ccc2NC1=O]

A solution of (S)-tert-butyl 1-(2-(4-fluorobenzoyl)-4-(trifluoromethoxy)phenylamino)-3-methyl-1-oxobutan-2-yl-carbamate/RO7040762-000-001/2 (323 mg, 648 µmol, Eq: 1.00) and trifluoroacetic acid (2.96 g, 2 ml, 26.0 mmol, Eq: 40.1) in dichloromethane (2 ml) was stirred for 1 hour at 60° C. The solvent was evaporated, the residue was diluted with ethyl acetate and washed with sodiumhydrogen carbonate sat. and brine. The organic layer was separated, dried over magnesium sulfate, filtrated and evaporated. The material was dissolved in toluene (25 ml) and refluxed for 18 hours overnight The crude material was applied on silica gel and purified by flash chromatography over a 20 g silicagel column using heptane/ethyl acetate 10-50% as eluent to give (167 mg, 67.8%) as a light yellow solid. M+H+=381.2 c) (S)-5-(4-Fluoro-phenyl)-3-isopropyl-7-trifluoromethoxy-1,3-dihydro-benzo[e][1,4]diazepine-2-thione A mixture of (S)-5-(4-fluorophenyl)-3-isopropyl-7-(trifluoromethoxy)-1H-benzo[e][1,4]diazepin-2(3H)-one (147 mg, 387 µmol, Eq: 1.00) and Lawesson's reagent (313 mg, 773 µmol, Eq: 2) in 1,2-dimethoxyethane (5 ml) was stirred for 18 hours at 80° C. in a closed microwave vessel. The crude material was applied on silica gel and purified by flash chromatography over a 20 g silicagel column using heptane/ethyl acetate 10-30% as eluent to give example 1 (109 mg, 71.1%) as a light yellow solid. M+H+=397.1

Example 2

(3S)-7-bromo-3-propan-2-yl-5-pyridin-2-yl-1,3-dihydro-1,4-benzodiazepine-2-thione a) tert-butyl N-[(1S)-1-[[4-bromo-2-(pyridine-2-carbonyl)phenyl]carbamoyl]-2-methyl-propyl]carbamate

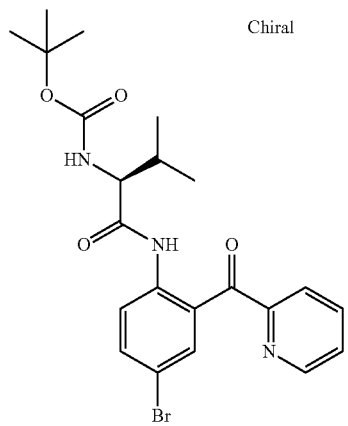 [SMILES: CC(C)[C@H](NC(=O)OC(C)(C)C)C(=O)Nc1ccc(Br)cc1C(=O)c1ccccn1]

The product was prepared in the same manner as in example 1a) using (2-amino-5-bromophenyl)(pyridin-2-yl)methanone (300 mg, 1.08 mmol, Eq: 1.00) and (S)-2-((tert-butoxycarbonyl)amino)-3-methylbutanoic acid (235 mg, 1.08 mmol, Eq: 1.00) as starting materials affording tert-butyl N-[(1S)-1-[[4-bromo-2-(pyridine-2-carbonyl)phenyl]carbamoyl]-2-methyl-propyl]carbamate (241 mg, 46.7% yield) as a light yellow oil. MS: m/z (M+H)+=478.11 b) (3S)-7-bromo-3-isopropyl-5-(2-pyridyl)-1,3-dihydro-1,4-benzodiazepin-2-one

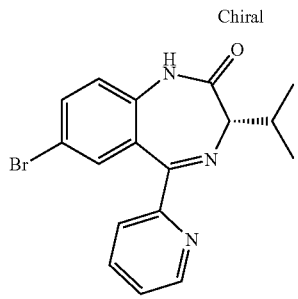 [SMILES: CC(C)[C@@H]1N=C(c2ccccn2)c2cc(Br)ccc2NC1=O]

The product was prepared in the same manner as in example 1b) using (S)-tert-butyl (1-((4-bromo-2-picolinoylphenyl)amino)-3-methyl-1-oxobutan-2-yl)carbamate (241 mg, 506 µmol, Eq: 1.00) as starting material affording (3S)-7-bromo-3-isopropyl-5-(2-pyridyl)-1,3-dihydro-1,4-benzodiazepin-2-one (161 mg, 88.8% yield) as a yellow foam. MS: m/z (M+H)+=358.1 c) (3S)-7-bromo-3-isopropyl-5-(2-pyridyl)-1,3-dihydro-1,4-benzodiazepine-2-thione To (S)-7-bromo-3-isopropyl-5-(pyridin-2-yl)-1H-benzo[e][1,4]diazepin-2(3H)-one (70 mg, 195 µmol, Eq: 1) in tetrahydrofuran (521 µl) was added sodium hydride (9.77 mg, 244 µmol, Eq: 1.25) at room temperature. The vial was sealed and stirring was continued for 20 min at 60° C. After cooling to room temperature dimorpholinophosphinic chloride (74.6 mg, 293 µmol, Eq: 1.5)[7] was added and the reaction was stirred at room temperature overnight. Triethylamine (39.5 mg, 54.2 µl, 391 µmol, Eq: 2) was added followed from hydrogen sulfide in THF 0.8M (2.44 ml, 1.95 mmol, Eq: 10) and stirring was continued at 50° C. overnight. Water was added and the yellow mixture was extracted three times with dichloromethane, dried over magnesium sulfate, filtered and evaporated. The crude material was applied on silica gel and purified by flash chromatography using hepate/ethyl acetate (0-40% ethyl acetate) as eluent affording example 2 (36 mg, 49.2% yield) as a yellow solid. MS: m/z (M+H)+=376.1

Example 3

(3S)-7-chloro-3-(cyclopropylmethyl)-5-phenyl-1,3-dihydro-1,4-benzodiazepine-2-thione a) (2-benzoyl-4-chloro-phenyl) (2S)-2-(tert-butoxy-carbonylamino)-3-cyclopropyl-propanoate

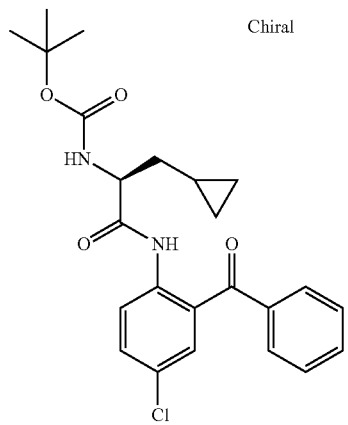 [SMILES: CC(C)(C)OC(=O)N[C@@H](CC1CC1)C(=O)Nc1ccc(Cl)cc1C(=O)c1ccccc1]

The product was prepared in the same manner as in example 1a) using (2-amino-5-chlorophenyl)(phenyl)methanone (700 mg, 3.02 mmol, Eq: 1.00) and (S)-2-(tert-butoxycarbonylamino)-3-cyclopropylpropanoic acid (693 mg, 3.02 mmol, Eq: 1.00) as starting materials affording (2-benzoyl-4-chloro-phenyl) (2S)-2-(tert-butoxycarbonylamino)-3-cyclopropyl-propanoate (953 mg, 71.1% yield) as a light brown foam. MS: m/z (M+H)+=445.2 b) (S)-7-Chloro-3-cyclopropylmethyl-5-phenyl-1,3-dihydro-benzo[e][1,4]diazepin-2-one

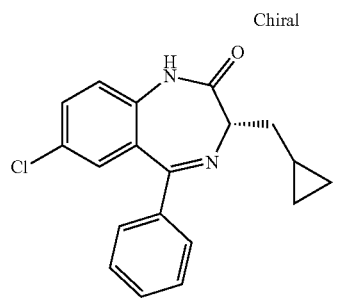 [SMILES: O=C1Nc2ccc(Cl)cc2C(c2ccccc2)=N[C@H]1CC1CC1]

The product was prepared in the same manner as in example 1b) using (S)-2-benzoyl-4-chlorophenyl 2-(tert-butoxycarbonylamino)-3-cyclopropylpropanoate (953 mg, 2.15 mmol, Eq: 1.00) as starting material affording (S)-7-Chloro-3-cyclopropylmethyl-5-phenyl-1,3-dihydro-benzo[e][1,4]diazepin-2-one (636 mg, 91.2% yield) as a light yellow foam. MS: m/z (M+H)+=325.1 c) (S)-7-Chloro-3-cyclopropylmethyl-5-phenyl-1,3-dihydro-benzo[e][1,4]diazepine-2-thione The product was prepared in the same manner as in example 1c) using (S)-7-chloro-3-(cyclopropylmethyl)-5-phenyl-1H-benzo[e][1,4]diazepin-2(3H)-one (150 mg, 462 µmol, Eq: 1.00) as starting material affording example 3 (72 mg, 45.7% yield) as a yellow viscous oil. MS: m/z (M+H)+=341.1

Example 4

(3S)-7-chloro-3-ethyl-5-phenyl-1,3-dihydro-1,4-benzodiazepine-2-thione a) tert-butyl N-[(1S)-1-[(2-benzoyl-4-chloro-phenyl)carbamoyl]propyl]carbamate

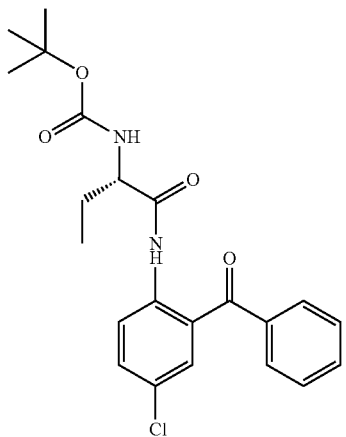

The product was prepared in the same manner as in example 1a) using (2-amino-5-chlorophenyl)(phenyl)methanone (500 mg, 2.16 mmol, Eq: 1.00) and (S)-2-(tert-butoxycarbonylamino)butanoic acid (439 mg, 2.16 mmol, Eq: 1.00) as starting material affording [(S)-1-(2-Benzoyl-4-chloro-phenylcarbamoyl)-propyl]-carbamic acid tert-butyl ester (976 mg, 108% yield) as an orange oil. MS: m/z (M−H)−=415.3 b) (S)-7-Chloro-3-ethyl-5-phenyl-1,3-dihydro-benzo[e][1,4]diazepin-2-one

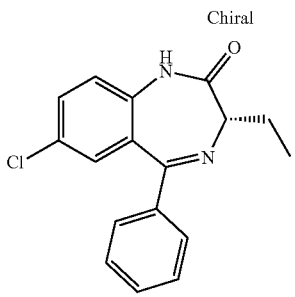 [SMILES: CC[C@@H]1N=C(c2ccccc2)c2cc(Cl)ccc2NC1=O]

The product was prepared in the same manner as in example 1b) using (S)-tert-butyl 1-(2-benzoyl-4-chlorophe nylamino)-1-oxobutan-2-ylcarbamate (900 mg, 2.16 mmol, Eq: 1.00) as starting material affording (S)-7-Chloro-3-ethyl-5-phenyl-1,3-dihydro-benzo[e][1,4]diazepin-2-one (602 mg, 93.3% yield) as light yellow foam. MS: m/z (M+H)+=299.1 c) (S)-7-Chloro-3-ethyl-5-phenyl-1,3-dihydro-benzo[e][1,4]diazepine-2-thione

The product was prepared in the same manner as in example 1c) using (S)-7-chloro-3-ethyl-5-phenyl-1H-benzo[e][1,4]diazepin-2(3H)-one (200 mg, 669 µmol, Eq: 1.00) as starting material affording example 4 (113 mg, 53.6% yield) as a white solid. MS: m/z (M+H)+=315.1

Example 5

(3S)-7-chloro-5-(2-fluorophenyl)-3-propan-2-yl-1,3-dihydro-1,4-benzodiazepine-2-thione The product was prepared in the same manner as in example 1 using (S)-7-chloro-5-(2-fluorophenyl)-3-isopropyl-1H-benzo[e][1,4]diazepin-2(3H)-one (600 mg, 1.81 mmol, Eq: 1.00) as starting material affording example 5 (282 mg, 44.8%) as light yellow solid. MS: m/z (M+H)+=347.2

Example 6

(3S)-7-chloro-3-methyl-5-phenyl-3-propyl-1H-1,4-benzodiazepine-2-thione a) (R)-7-chloro-3-methyl-5-phenyl-1H-benzo[e][1,4]diazepin-2(3H)-one

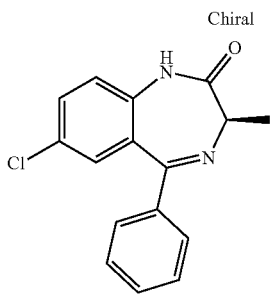 [SMILES: C[C@H]1N=C(c2ccccc2)c2cc(Cl)ccc2NC1=O]

Chiral

The product was prepared in the same manner as in example 1 using (R)-tert-butyl (1-((2-benzoyl-4-chlorophenyl)amino)-1-oxopropan-2-yl)carbamate (1.45 g, 3.6 mmol, Eq: 1.00) as starting material affording (R)-7-chloro-3-methyl-5-phenyl-1H-benzo[e][1,4]diazepin-2(3H)-one (1 g, 3.51 mmol, 97.6% yield) as a light yellow oil. MS: m/z (M+H)+=285.08 b) (R)-7-chloro-1-(4-methoxybenzyl)-3-methyl-5-phenyl-1H-benzo[e][1,4]diazepin-2(3H)-one

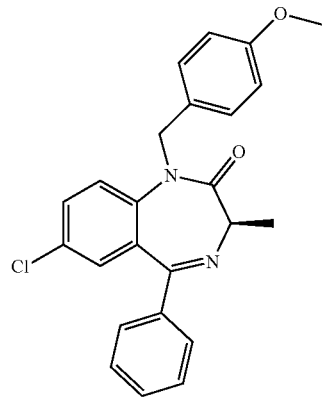 [SMILES: COc1ccc(CN2C(=O)[C@@H](C)N=C(c3ccccc3)c3cc(Cl)ccc32)cc1]

To a solution of (R)-7-chloro-3-methyl-5-phenyl-1H-benzo[e][1,4]diazepin-2(3H)-one (1 g, 3.51 mmol, Eq: 1.00) in tetrahydrofuran (16 ml) under argon atmosphere was added portionwise sodium hydride (162 mg, 4.04 mmol, Eq: 1.15). The mixture was stirred for 30 minutes at 0° C., then 1-(chloromethyl)-4-methoxybenzene (825 mg, 714 µl, 5.27 mmol, Eq: 1.5) was added and the cooling bath was removed and the reaction was allowed to warm slowly to 25° C. and stirred for 4 h. LCMS showed just starting material. Stirring was continued over night at room temperature. Just very little product peak and lot of starting material left. sodium hydride (42.1 mg, 1.76 mmol, Eq: 0.5) was slowly added (after cooling to 0° C.) in one portion. After stirring for 30 min. 1-(chloromethyl)-4-methoxybenzene (275 mg, 238 µl 1.76 mmol, Eq: 0.5) was added in one portion. The mixture was allowed to reach room temperature and stirring was continued for two days. The crude material was applied on silicagel and purified by flash chromatography using heptane/ethyl acetate (10-30% ethyl acetate) as eluent affording (R)-7-chloro-1-(4-methoxybenzyl)-3-methyl-5-phenyl-1H-benzo[e][1,4]diazepin-2(3H)-one (1.035 g, 72.8%) as white foam. MS: m/z (M+H)+=405.13 c) 3-allyl-7-chloro-1-[(4-methoxyphenyl)methyl]-3-methyl-5-phenyl-1,4-benzodiazepin-2-one

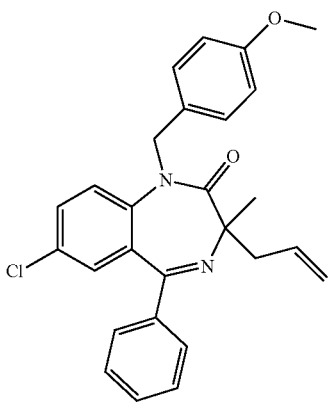 [SMILES: C=CCC1(C)N=C(c2ccccc2)c2cc(Cl)ccc2N(Cc2ccc(OC)cc2)C1=O]

To a solution of diisopropylamine (120 mg, 169 μl, 1.19 mmol, Eq: 1.2) in tetrahydrofuran (6.5 ml) was added n-butyllithium (741 μl, 1.19 mmol, Eq: 1.2) at −15° C. under argon atmosphere, the mixture was allowed to reach 0° C. and stirred for 15 minutes, then cooled to −78° C. and tris(N,N-tetramethylene)phosphoric acid triamide (1.53 g, 1.36 ml, 5.93 mmol, Eq: 6) was added (after addition not stirrable), the mixture stayed for 15 minutes, then n-butyllithium (741 μl, 1.19 mmol, Eq: 1.2) (while addition stirrable again) followed by a solution of (R)-7-chloro-1-(4-methoxybenzyl)-3-methyl-5-phenyl-1H-benzo[e][1,4]diazepin-2 (3H)-one (400 mg, 988 μmol, Eq: 1.00) in tetrahydrofuran (6.5 ml) was added (turned deep red), and the mixture was stirred for 15 minutes, then the allylbromide (1.2 g, 836 μl, 9.88 mmol, Eq: 10) was added and stirring at −78° C. was continued for 2 hours. LCMS showed new product formed along with some other peaks. The mixture was quenched by the addition of ammoniumchloride sol. sat. and extracted with ethyl acetate, the organic layer was combined, washed with water and brine, dried over magnesium sulfate filtrated and evaporated. The crude material was applied on silicagel and purified by flash chromatography over a 20 g silicagel column using heptane/ethyl acetate 5-20% as eluent affording 3-allyl-7-chloro-1-(4-methoxybenzyl)-3-methyl-5-phenyl-1H-benzo[e][1,4]diazepin-2(3H)-one (150 mg, 337 μmol, 34.1% yield) as a light brown oil. This material was directly used in the next step.

d) 7-chloro-1-[(4-methoxyphenyl)methyl]-3-methyl-5-phenyl-3-propyl-1,4-benzodiazepin-2-one

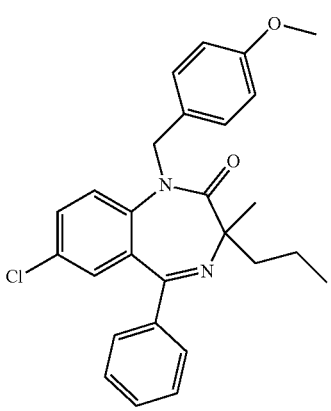 [SMILES: CCCC1(C)N=C(c2ccccc2)c2cc(Cl)ccc2N(Cc2ccc(OC)cc2)C1=O]

3-allyl-7-chloro-1-(4-methoxybenzyl)-3-methyl-5-phenyl-1H-benzo[e][1,4]diazepin-2(3H)-one (140 mg, 315 μmol, Eq: 1.00) was stirred in methanol with palladium 5% on barium sulfate (17.4 mg, 8.17 μmol, Eq: 0.026) under a hydrogen atmosphere for 2 h. The catalyst was filtered off and washed with little methanol. The solvent was evaporated and the crude material was applied on silica gel and purified by column chromatography using heptane/ethyl acetate (0-40% ethyl acetate) as eluent affording 7-chloro-1-(4-methoxybenzyl)-3-methyl-5-phenyl-3-propyl-1H-benzo[e][1,4]diazepin-2(3H)-one (135 mg, 302 μmol, 96% yield) as a light yellow oil. MS: m/z (M+H)+=447.3 e) 7-chloro-3-methyl-5-phenyl-3-propyl-1H-1,4-benzodiazepin-2-one

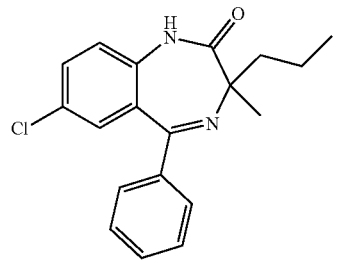 [SMILES: CCCC1(C)N=C(c2ccccc2)c2cc(Cl)ccc2NC1=O]

A mixture of 7-chloro-1-(4-methoxybenzyl)-3-methyl-5-phenyl-3-propyl-1H-benzo[e][1,4]diazepin-2(3H)-one (130 mg, 291 μmol, Eq: 1.00), trifluoromethanesulfonic acid (436 mg, 258 μl, 2.91 mmol, Eq: 10) and trifluoroacetic acid (995 mg, 672 μl, 8.73 mmol, Eq: 30) in dichloromethane (3.5 ml) (very dark mixture, immediately) was stirred overnight at 25° C. The mixture was diluted with dichloromethane and washed with sodiumhydrogen carbonate sat. and brine. The organic layer was separated, dried over magnesium sulfate, filtrated and evaporated. The crude material was applied on silicagel and purified by flash chromatography using heptane/ethyl acetate 10-40% as eluent affording 7-chloro-3-methyl-5-phenyl-3-propyl-1H-1,4-benzodiazepin-2-one (75 mg, 78.9%) as a light yellow oil. MS: m/z (M+H)+=327.13 f) (S)-7-Chloro-3-methyl-5-phenyl-3-propyl-1,3-dihydro-benzo[e][1,4]diazepine-2-thione The product was prepared in the same manner as in example 5c) using 7-chloro-3-methyl-5-phenyl-3-propyl-1H-benzo[e][1,4]diazepin-2(3H)-one (70 mg, 214 μmol, Eq: 1.00) as starting material affording example 6 (12 mg, 16.3%) as off white solid. MS: m/z (M+H)+=343.2

Example 7

(3S)-7-chloro-5-phenyl-3-propyl-1,3-dihydro-1,4-benzodiazepine-2-thione a) tert-butyl N-[(1S)-1-[(2-benzoyl-4-chloro-phenyl)carbamoyl]butyl]carbamate

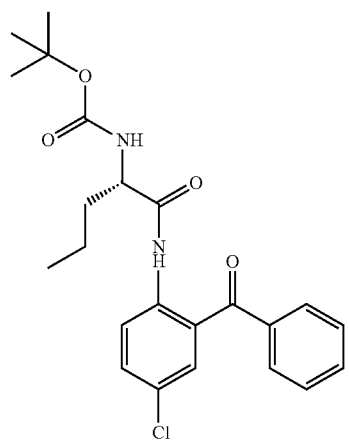 [SMILES: CCC[C@H](NC(=O)OC(C)(C)C)C(=O)Nc1ccc(Cl)cc1C(=O)c1ccccc1]

The product was prepared in the same manner as in example 1a) using (2-amino-5-chlorophenyl)(phenyl)methanone (500 mg, 2.16 mmol, Eq: 1.00) and (S)-2-(tert-butoxycarbonylamino)pentanoic acid (469 mg, 2.16 mmol, Eq: 1.00) as starting materials affording tert-butyl N-[(1S)-1-[(2-benzoyl-4-chloro-phenyl)carbamoyl]butyl]carbamate (713 mg, 76.7% yield) as a yellow solid. MS: m/z (M–H)–=429.3 b) (S)-3-Isopropyl-5,7-diphenyl-1,3-dihydro-benzo[e][1,4]diazepin-2-one

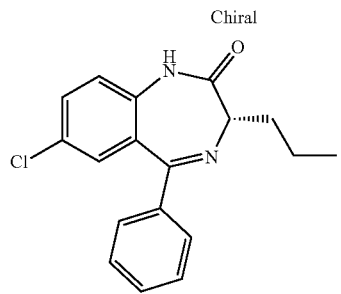 [SMILES: CCC[C@@H]1N=C(c2ccccc2)c2cc(Cl)ccc2NC1=O]

The product was prepared in the same manner as in example 1b) using (S)-tert-butyl 1-(2-benzoyl-4-chlorophenylamino)-1-oxopentan-2-ylcarbamate (700 mg, 1.62 mmol, Eq: 1.00) as starting material affording (S)-3-Isopropyl-5,7-diphenyl-1,3-dihydro-benzo[e][1,4]diazepin-2-one (940 mg, 102% yield) as a light brown solid. MS: m/z (M+H)+=313.1 c) (S)-7-Chloro-5-phenyl-3-propyl-1,3-dihydro-benzo[e][1,4]diazepine-2-thione

The product was prepared in the same manner as in example 1c) using (S)-7-chloro-5-phenyl-3-propyl-1H-benzo[e][1,4]diazepin-2(3H)-one (150 mg, 480 μmol, Eq: 1.00) as starting material affording example 7 (93 mg, 59% yield) as a white solid. MS: m/z (M+H)+=329.1

Example 8

(3S)-7-chloro-5-phenyl-3-(2,2,2-trifluoroethyl)-1,3-dihydro-1,4-benzodiazepine-2-thione a) tert-butyl N-[(1S)-1-[(2-benzoyl-4-chloro-phenyl)carbamoyl]-3,3,3-trifluoro-propyl]carbamate

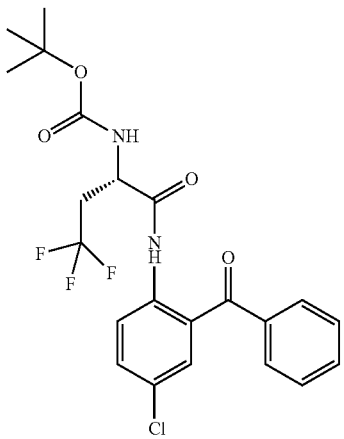 [SMILES: CC(C)(C)OC(=O)N[C@@H](CC(F)(F)F)C(=O)Nc1ccc(Cl)cc1C(=O)c1ccccc1]

The product was prepared in the same manner as in example 1a) using (2-amino-5-chlorophenyl)(phenyl)methanone (500 mg, 2.16 mmol, Eq: 1.00) and (S)-2-(tert-butoxycarbonylamino)-4,4,4-trifluorobutanoic acid (555 mg, 2.16 mmol, Eq: 1.00) as starting materials affording tert-butyl N-[(1S)-1-[(2-benzoyl-4-chloro-phenyl)carbamoyl]-3,3,3-trifluoro-propyl]carbamate (1.01 g, 99.4% yield) as a yellow solid. MS: m/z (M–H)–=469.3 b) (S)-7-Chloro-5-phenyl-3-(2,2,2-trifluoro-ethyl)-1,3-dihydro-benzo[e][1,4]diazepin-2-one

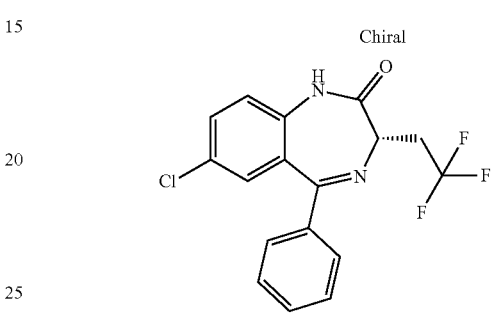

The product was prepared in the same manner as in example 1b) using (S)-tert-butyl 1-(2-benzoyl-4-chlorophenylamino)-4,4,4-trifluoro-1-oxobutan-2-ylcarbamate (1.01 g, 2.14 mmol, Eq: 1.00) as starting material affording (S)-7-Chloro-5-phenyl-3-(2,2,2-trifluoro-ethyl)-1,3-dihydro-benzo[e][1,4]diazepin-2-one (770 mg, 102% yield) as a yellow amorphous. MS: m/z (M+H)+=353.1 c) (S)-7-Chloro-5-phenyl-3-(2,2,2-trifluoro-ethyl)-1,3-dihydro-benzo[e][1,4]diazepine-2-thione

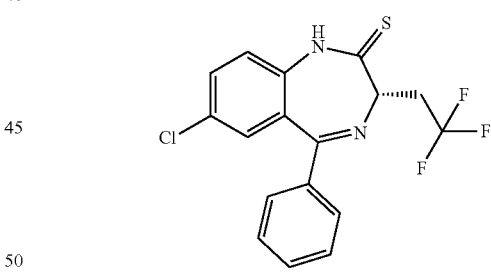

The product was prepared in the same manner as in example 1c) using (S)-7-chloro-5-phenyl-3-(2,2,2-trifluoro-ethyl)-1H-benzo[e][1,4]diazepin-2(3H)-one (200 mg, 567 μmol, Eq: 1.00) as starting material affording example 8 (152 mg, 72.7% yield) as an off-white solid. MS: m/z (M+H)+=369.1

Example 9

(3R)-7-chloro-3-(2-methylsulfanylethyl)-5-phenyl-1,3-dihydro-1,4-benzodiazepine-2-thione The product was prepared in the same manner as in example 1c) using (R)-7-chloro-3-(2-(methylthio)ethyl)-5-phenyl-1H-benzo[e][1,4]diazepin-2(3H)-one (50 mg, 145

μmol, Eq: 1.00) as starting material affording example 9 (28 mg, 53.5%) as a light yellow solid. MS: m/z (M+H)+=361.1

Example 10

(3S)-7-chloro-5-(2-fluorophenyl)-3-(trifluoromethyl)-1,3-dihydro-1,4-benzodiazepine-2-thione a) 7-chloro-5-(2-fluorophenyl)-3-(trifluoromethyl)-1,3-dihydro-1,4-benzodiazepin-2-one

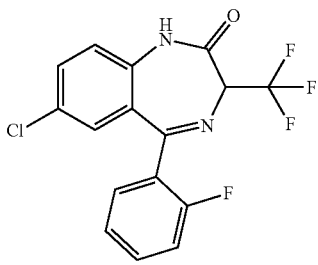 [SMILES: O=C1Nc2ccc(Cl)cc2C(c2ccccc2F)=NC1C(F)(F)F]

The product was prepared in the same manner as in example 1b) using tert-butyl 3-(4-chloro-2-(2-fluorobenzoyl)phenylamino)-1,1,1-trifluoro-3-oxopropan-2-ylcarbamate (464 mg, 977 μmol, Eq: 1.00) as starting material affording 7-Chloro-5-(2-fluoro-phenyl)-3-trifluoromethyl-1,3-dihydro-benzo[e][1,4]diazepin-2-one (229 mg, 65.7% yield) as an off-white foam. MS: m/z (M+H)+=357.1 b) (3R)-7-chloro-5-(2-fluorophenyl)-3-(trifluoromethyl)-1,3-dihydro-1,4-benzodiazepin-2-one

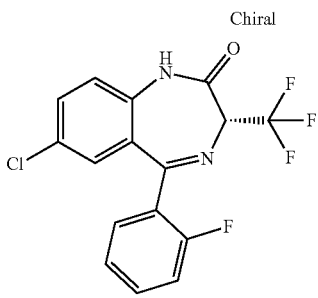 [SMILES: O=C1Nc2ccc(Cl)cc2C(c2ccccc2F)=N[C@H]1C(F)(F)F]

Chiral separation of racemic 7-chloro-5-(2-fluorophenyl)-3-(trifluoromethyl)-1H-benzo[e][1,4]diazepin-2(3H)-one (213 mg, 597 μmol) affording (3R)-7-chloro-5-(2-fluorophenyl)-3-(trifluoromethyl)-1,3-dihydro-1,4-benzodiazepin-2-one (96 mg, 45.1% yield) as a white solid. MS: m/z (M+H)+=357.1 c) (S)-7-chloro-5-(2-fluorophenyl)-3-(trifluoromethyl)-1H-benzo[e][1,4]diazepine-2(3H)-thione The product was prepared in the same manner as in example 1c) using (R)-7-chloro-5-(2-fluorophenyl)-3-(trifluoromethyl)-1H-benzo[e][1,4]diazepin-2(3H)-one (90 mg, 252 μmol, Eq: 1.00) as starting material affording example 10 (30 mg, 31.9% yield) as a light yellow solid. MS: m/z (M+H)+=373.1

Example 11

(3R)-7-chloro-5-(2-fluorophenyl)-3-(trifluoromethyl)-1,3-dihydro-1,4-benzodiazepine-2-thione The product was prepared in the same manner as in example 13 using other enantiomer (S)-7-chloro-5-(2-fluorophenyl)-3-(trifluoromethyl)-1H-benzo[e][1,4]diazepin-2(3H)-one (90 mg, 252 μmol, Eq: 1.00) as starting material affording example 11 (30 mg, 31.9% yield) as a yellow solid. MS: m/z (M+H)+=373.1

Example 12

3-methyl-7-nitro-5-phenyl-1,3-dihydro-1,4-benzodiazepine-2-thione

The product was prepared in the same manner as in example 1c) using 3-methyl-7-nitro-5-phenyl-1H-benzo[e][1,4]diazepin-2(3H)-one (50 mg, 169 μmol, Eq: 1.00) as starting material affording example 12 (15 mg, 28.5% yield) as a yellow solid. MS: m/z (M+H)+=312.2

Example 13

(3S)-5-(2-fluorophenyl)-3-isopropyl-7-methyl-1,3-dihydro-1,4-benzodiazepine-2-thione a) tert-butyl N-[(1S)-1-[[2-(2-fluorobenzoyl)-4-methyl-phenyl]carbamoyl]-2-methyl-propyl]carbamate

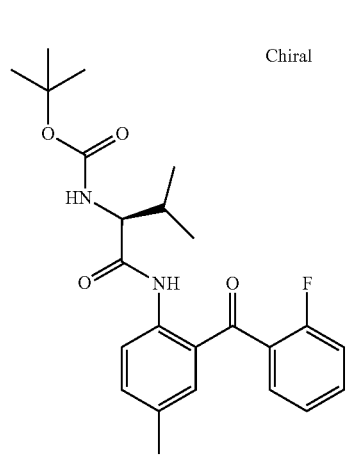 [SMILES: Cc1ccc(NC(=O)[C@@H](NC(=O)OC(C)(C)C)C(C)C)c(C(=O)c2ccccc2F)c1]

The product was prepared in the same manner as in example 1a) using (2-amino-5-methylphenyl)(2-fluorophenyl)methanone (400 mg, 1.74 mmol, Eq: 1) and (S)-2-((tert-butoxycarbonyl)amino)-3-methylbutanoic acid (379 mg, 1.74 mmol, Eq: 1) as starting materials affording tert-butyl N-[(1 S)-1-[[2-(2-fluorobenzoyl)-4-methyl-phenyl]carbamoyl]-2-methyl-propyl]carbamate (390 mg, 52.2% yield) as a light yellow foam. MS: m/z (M−H)−=427.4 b) (3S)-5-(2-fluorophenyl)-3-isopropyl-7-methyl-1,3-dihydro-1,4-benzodiazepin-2-one

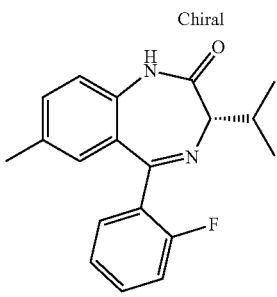 [SMILES: Cc1ccc2c(c1)C(c1ccccc1F)=N[C@@H](C(C)C)C(=O)N2]

The product was prepared in the same manner as in example 1b) using (S)-tert-butyl (1-((2-(2-fluorobenzoyl)-4-methylphenyl)amino)-3-methyl-1-oxobutan-2-yl)carbamate (390 mg, 910 µmol, Eq: 1) as starting material affording (3S)-5-(2-fluorophenyl)-3-isopropyl-7-methyl-1,3-dihydro-1,4-benzodiazepin-2-one (297 mg, 105% yield) as a yellow foam. MS: m/z (M+H)+=311.2 c) (3S)-5-(2-fluorophenyl)-3-isopropyl-7-methyl-1,3-dihydro-1,4-benzodiazepine-2-thione The product was prepared in the same manner as in example 5c) using (S)-5-(2-fluorophenyl)-3-isopropyl-7-methyl-1H-benzo[e][1,4]diazepin-2(3H)-one (295 mg, 950 µmol, Eq: 1) as starting material affording example 13 (101 mg, 32.6% yield) as a light yellow solid. MS: m/z (M+H)+=327.2

Example 14

[7-chloro-5-(2-fluorophenyl)-2-thioxo-1,3-dihydro-1-benzazepin-3-yl]acetate a) 3-bromo-7-chloro-5-(2-fluorophenyl)-1,3-dihydro-1-benzazepin-2-one

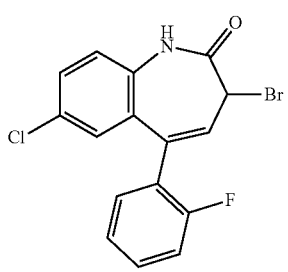 [SMILES: O=C1Nc2ccc(Cl)cc2C(c2ccccc2F)=CC1Br]

7-chloro-5-(2-fluorophenyl)-1,3-dihydro-1-benzazepin-2-one (EP72029) (1.44 g, 5 mmol) dissolved in tetrachloromethane (100 ml) are treated with bromine (0.26 ml, 5 mmol) and heated under irradiation with light for 30 minutes. All volatile components are removed and the remaining solid is chromatographed (100 g silica) with toluene. The afforded material is then recrystallized from diethylether-diisopropylether affording 3-bromo-7-chloro-5-(2-fluorophenyl)-1,3-dihydro-1-benzazepin-2-one (820 mg, 45% yield) as white crystals. Mp. 204-206° C. MS: m/z (M+)=365 b) [7-chloro-5-(2-fluorophenyl)-2-oxo-1,3-dihydro-1-benzazepin-3-yl]acetate

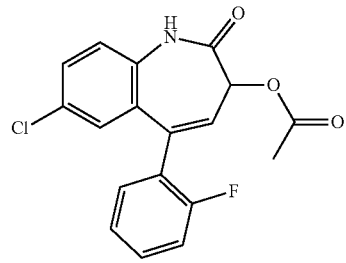 [SMILES: CC(=O)OC1C=C(c2ccccc2F)c2cc(Cl)ccc2NC1=O]

3-bromo-7-chloro-5-(2-fluorophenyl)-1,3-dihydro-1-benzazepin-2-one (733 mg, 2 mmol), sodium acetate (308 mg, 3.76 mmol) and glacial acetic acid (25 ml) are heated under reflux for 90 minutes. Volatile components are removed in vacuo and the remaining solid is treated with water. The aqueous phase is extracted twice with chloroform/ethanol 9:1. The combined organic layers are extracted with saturated aqueous sodium hydrogen carbonate, dried with sodium sulfate and evaporated to dryness. Recrystallization from ethyl acetate yields [7-chloro-5-(2-fluorophenyl)-2-oxo-1,3-dihydro-1-benzazepin-3-yl]acetate (567 mg, 82%) as colorless crystals. Mp. 240-242° C. MS: m/z (M+)=345 c) [7-chloro-5-(2-fluorophenyl)-2-thioxo-1,3-dihydro-1-benzazepin-3-yl]acetate

The product was prepared in the same manner as in example 1c) using [7-chloro-5-(2-fluorophenyl)-2-oxo-1,3-dihydro-1-benzazepin-3-yl]acetate (50 mg, 169 µmol, Eq: 1.00) as starting material and HMPT as solvent. Recrystallization from diisopropylether affords example 14 as light yellow crystals (50 mg, 85%). Mp 214-215° C. MS: m/z (M+)=361

Example 15

7-chloro-3-isopropyl-5-phenyl-1,3-dihydro-1,4-benzodiazepine-2-thione

The product was prepared in the same manner as in example 1c) using 7-chloro-3-isopropyl-5-phenyl-1H-benzo[e][1,4]diazepin-2(3H)-one (149 mg, 476 µmol, Eq: 1.00) as starting material affording example 15 (80 mg, 51.1% yield) as a light yellow foam. MS: m/z (M+H)+=329.1

Example 16

(3S)-7-chloro-3-isopropyl-5-phenyl-1,3-dihydro-1,4-benzodiazepine-2-thione

The product was prepared in the same manner as in example 1c) using (S)-7-chloro-3-isopropyl-5-phenyl-1H-benzo[e][1,4]diazepin-2(3H)-one (600 mg, 1.92 mmol, Eq: 1.00) as starting material affording (example 16 (520 mg, 82.4%) as light yellow solid. MS: m/z (M+H)+=329.1

Example 17

7-chloro-5-propyl-1,3-dihydro-1,4-benzodiazepine-2-thione

The product was prepared in the same manner as in example 1 using 7-chloro-5-propyl-1,3-dihydro-1,4-benzodiazepin-2-one (FR1391752, 172 mg, 554 µmol, Eq: 1.00) as starting material affording example 17.

Example 18

(3S)-3-isopropyl-5-phenyl-7-(trifluoromethyl)-1,3-dihydro-1,4-benzodiazepine-2-thione The product was prepared in the same manner as in example 1 using (S)-3-isopropyl-5-phenyl-7-(trifluoromethyl)-1H-benzo[e][1,4]diazepin-2(3H)-one (1.83 g, 5.28 mmol, Eq: 1.00) as starting material affording example 18 (535 mg, 27.9%) as light yellow foam. MS: m/z (M+H)+=363.115

Example 19

(3S)-3-isopropyl-5,7-diphenyl-1,3-dihydro-1,4-benzodiazepine-2-thione

The product was prepared in the same manner as in example 1 using (S)-3-isopropyl-5,7-diphenyl-1H-benzo[e][1,4]diazepin-2(3H)-one (150 mg, 423 µmol, Eq: 1.00) as starting material affording example 19 (40 mg, 25.5%) as light yellow solid. MS: m/z (M+H)+=371.2

Example 20

5-cyclohexyl-7-(trifluoromethyl)-1,3-dihydro-1,4-benzodiazepine-2-thione

The product was prepared in the same manner as in example 1 using 5-cyclohexyl-7-(trifluoromethyl)-1H-benzo[e][1,4]diazepin-2(3H)-one (prepared in analogy to U.S. Pat. No. 3,933,794, 172 mg, 554 µmol, Eq: 1.00) as starting material affording example 20 (104 mg, 57.5%) as light yellow solid. MS: m/z (M+H)+=327.2

Example 21

(3R)-3-benzyl-7-chloro-5-phenyl-1,3-dihydro-1,4-benzodiazepine-2-thione a) 3-benzyl-7-chloro-5-phenyl-1,3-dihydro-1,4-benzodiazepine-2-thione

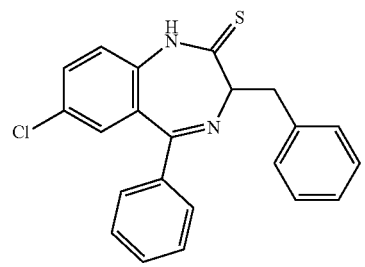 [SMILES: S=C1Nc2ccc(Cl)cc2C(c2ccccc2)=NC1Cc1ccccc1]

The product was prepared in the same manner as in example 1c using 3-benzyl-7-chloro-5-phenyl-1H-benzo[e][1,4]diazepin-2(3H)-one (200 mg, 554 µmol, Eq: 1.00) as starting material affording 3-benzyl-7-chloro-5-phenyl-1H-benzo[e][1,4]diazepine-2(3H)-thione (111 mg, 53.1%) as yellow solid. MS: m/z (M+H)+=377.0894 b) (3R)-3-benzyl-7-chloro-5-phenyl-1,3-dihydro-1,4-benzodiazepine-2-thione

The enantiomers where separated by chiral HPLC affording example 21 as the second eluting (−) isomer (62 mg, 56.4% yield) as a light yellow foam. MS: m/z (M+H)+=377.09

Example 22

(3S)-7-chloro-5-(3-chlorophenyl)-3-isopropyl-1,3-dihydro-1,4-benzodiazepine-2-thione a) tert-butyl N-[(1S)-1-[[4-chloro-2-(3-chlorobenzoyl)phenyl]carbamoyl]-2-methyl-propyl]carbamate

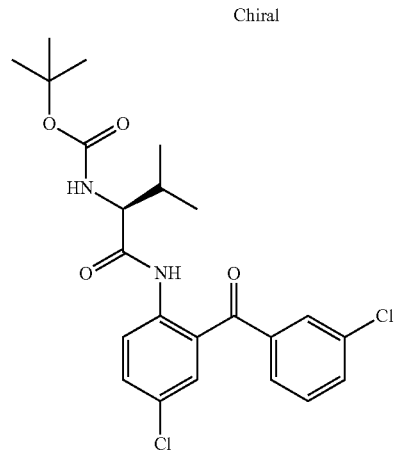 [SMILES: CC(C)[C@H](NC(=O)OC(C)(C)C)C(=O)Nc1ccc(Cl)cc1C(=O)c1cccc(Cl)c1]

The product was prepared in the same manner as in example 1a) using (2-amino-5-chlorophenyl)(3-chlorophenyl)methanone (300 mg, 1.13 mmol, Eq: 1.00) (WO2013/64465) and (S)-2-((tert-butoxycarbonyl)amino)-3-methylbutanoic acid (245 mg, 1.13 mmol, Eq: 1.00) as starting materials affording tert-butyl N-[(1S)-1-[[4-chloro-2-(3-chlorobenzoyl)phenyl]carbamoyl]-2-methyl-propyl]carbamate (442 mg, 84.3% yield) as a yellow foam. MS: m/z (M−H)−=463.4 b) (3S)-7-chloro-5-(3-chlorophenyl)-3-isopropyl-1,3-dihydro-1,4-benzodiazepin-2-one

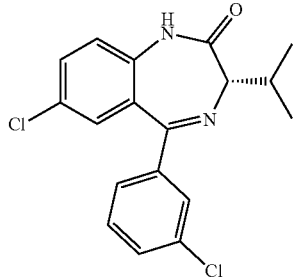 [SMILES: CC(C)[C@@H]1N=C(c2cccc(Cl)c2)c2cc(Cl)ccc2NC1=O]

The product was prepared in the same manner as in example 1b) using (S)-tert-butyl (1-((4-chloro-2-(3-chlorobenzoyl)phenyl)amino)-3-methyl-1-oxobutan-2-yl)carbamate (338 mg, 726 µmol, Eq: 1.00) as starting material affording (3S)-7-chloro-5-(3-chlorophenyl)-3-isopropyl-1,3-dihydro-1,4-benzodiazepin-2-one (269 mg, 107% yield) as a yellow oil. MS: m/z (M+H)+=347.2 c) (3S)-7-chloro-5-(3-chlorophenyl)-3-isopropyl-1,3-dihydro-1,4-benzodiazepine-2-thione The product was prepared in the same manner as in example 5c) using (S)-7-chloro-5-(3-chlorophenyl)-3-isopropyl-1H-benzo[e][1,4]diazepin-2(3H)-one (260 mg, 749 µmol, Eq: 1) as starting material affording example 22 (114 mg, 41.9% yield) as a yellow solid. MS: m/z (M+H)+=363.1

Example 23

(3S)-8-chloro-5-(2-fluorophenyl)-3-isopropyl-1,3-dihydro-1,4-benzodiazepine-2-thione a) 2-Amino-4-chloro-phenyl-(2-fluoro-phenyl)-methanone

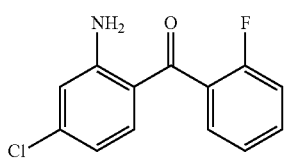 [SMILES: Nc1cc(Cl)ccc1C(=O)c1ccccc1F]

To gallium (III) chloride 1M in 1,2-dichloroethane (10.0 ml, 10 mmol, Eq: 0.850) was added under argon atmosphere 3-chloroaniline (1.5 g, 1.25 ml, 11.8 mmol, Eq: 1.00) keeping the temperature below 5° C. (exothermic). After the addition the mixture was cooled to −10° C. and boron trichloride 1M in dichloromethane (8.82 ml, 8.82 mmol, Eq: 0.75) was added while keeping the temperature below −5° C. (exothermic). Finally the 2-fluorobenzonitrile (1.42 g, 1.28 ml, 11.8 mmol, Eq: 1) was added (exothermic) and the mixture was allowed to warm to 25° C. The mixture was then refluxed for 18 hours at 80° C. The mixture was cooled with ice and hydrolized with water (ca 10 ml). The resulting mixture was then heated for 1.5 hours to 80° C. The mixture was diluted with dichloromethane and washed with sodium carbonate sat., the organic layer was separated, dried over magnesium sulfate, filtrated and evaporated. The material was applied on silicagel and purified by flash chromatography using heptane/ethyl acetate (5-20% ethyl acetate) as eluent affording 2-Amino-4-chloro-phenyl)-(2-fluoro-phenyl)-methanone (841 mg, 28.6% yield) as a yellow solid. MS: m/z (M+H)+=250.1 b) (S)-Tert-butyl 1-(5-chloro-2-(2-fluorobenzoyl)phenylamino)-3-methyl-1-oxobutan-2-ylcarbamate

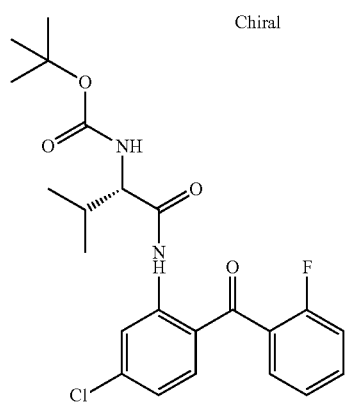 [SMILES: CC(C)[C@H](NC(=O)OC(C)(C)C)C(=O)Nc1cc(Cl)ccc1C(=O)c1ccccc1F]

The product was prepared in the same manner as in example 1a) using (2-amino-4-chlorophenyl)(2-fluorophenyl)methanone (300 mg, 1.2 mmol, Eq: 1.00) and (S)-2-(tert-butoxycarbonylamino)-3-methylbutanoic acid (261 mg, 1.2 mmol, Eq: 1.00) as starting materials affording (S)-tert-butyl 1-(5-chloro-2-(2-fluorobenzoyl)phenylamino)-3-methyl-1-oxobutan-2-ylcarbamate (380 mg, 70.4% yield) as a red viscous oil. MS: m/z (M+H)+=447.3 c) (S)-8-Chloro-5-(2-fluoro-phenyl)-3-isopropyl-1,3-dihydro-benzo[e][1,4]diazepin-2-one

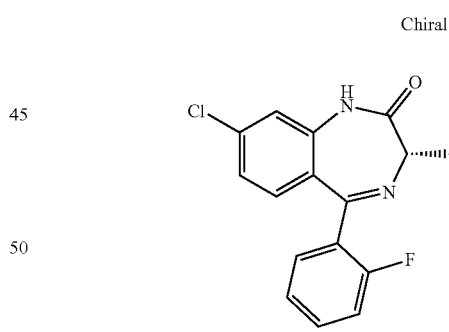

The product was prepared in the same manner as in example 1b) using (S)-tert-butyl 1-(5-chloro-2-(2-fluorobenzoyl)phenylamino)-3-methyl-1-oxobutan-2-ylcarbamate (380 mg, 846 µmol, Eq: 1.00) as starting material affording (S)-8-Chloro-5-(2-fluoro-phenyl)-3-isopropyl-1,3-dihydro-benzo[e][1,4]diazepin-2-one (244 mg, 87.1% yield) as a light brown foam. MS: m/z (M+H)+=331.1 d) (S)-8-Chloro-5-(2-fluoro-phenyl)-3-isopropyl-1,3-dihydro-benzo[e][1,4]diazepine-2-thione The product was prepared in the same manner as in example 1c) using (S)-8-chloro-5-(2-fluorophenyl)-3-isopropyl-1H-benzo[e][1,4]diazepin-2(3H)-one (234 mg, 707 µmol, Eq: 1.00) as starting material affording example 23 (70 mg, 28.5% yield) as a yellow viscous oil. MS: m/z (M+H)+=347.1

Example 24

(3S)-7-chloro-3-cyclopropyl-5-phenyl-1,3-dihydro-1,4-benzodiazepine-2-thione a) (S)-tert-butyl 2-(2-benzoyl-4-chlorophenylamino)-1-cyclopropyl-2-oxoethylcarbamate

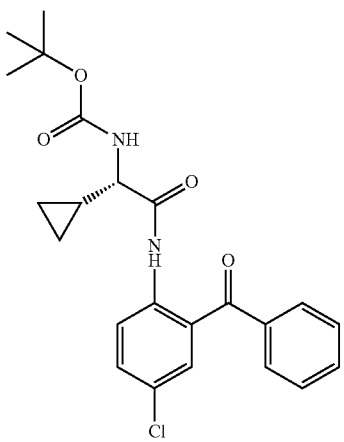 [SMILES: CC(C)(C)OC(=O)N[C@H](C(=O)Nc1ccc(Cl)cc1C(=O)c1ccccc1)C1CC1]

The product was prepared in the same manner as in example 1a) using (2-amino-5-chlorophenyl)(phenyl)methanone (500 mg, 2.16 mmol, Eq: 1.00) and (S)-2-(tert-butoxycarbonylamino)-2-cyclopropylacetic acid (465 mg, 2.16 mmol, Eq: 1.00) as starting materials affording (S)-tert-butyl 2-(2-benzoyl-4-chlorophenylamino)-1-cyclopropyl-2-oxoethylcarbamate (940 mg, 102%) as a yellow foam. MS: m/z (M−H)−=427.3 b) (S)-7-Chloro-3-cyclopropyl-5-phenyl-1,3-dihydro-benzo[e][1,4]diazepin-2-one

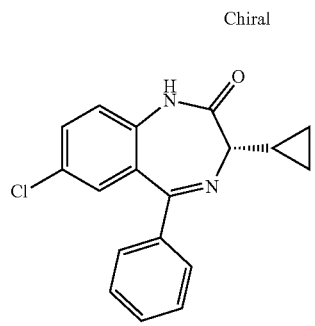 [SMILES: O=C1Nc2ccc(Cl)cc2C(c2ccccc2)=N[C@H]1C1CC1]

The product was prepared in the same manner as in example 1b) using (S)-tert-butyl 2-(2-benzoyl-4-chlorophenylamino)-1-cyclopropyl-2-oxoethylcarbamate (940 mg, 2.19 mmol, Eq: 1.00) as starting material affording (S)-7-Chloro-3-cyclopropyl-5-phenyl-1,3-dihydro-benzo[e][1,4]diazepin-2-one (670 mg, 98.4% yield) as light yellow solid. MS: m/z (M+H)+=311.1 c) (S)-7-Chloro-3-cyclopropyl-5-phenyl-1,3-dihydro-benzo[e][1,4]diazepine-2-thione The product was prepared in the same manner as in example 1c) using (S)-7-chloro-3-cyclopropyl-5-phenyl-1H-benzo[e][1,4]diazepin-2(3H)-one (200 mg, 644 µmol, Eq: 1.00) as starting material affording example 24 (106 mg, 50.4%) as white solid. MS: m/z (M+H)+=327.1

Example 25

(3S)-3-isopropyl-5-phenyl-7-(trifluoromethoxy)-1,3-dihydro-1,4-benzodiazepine-2-thione a) tert-butyl N-[(1S)-1-[[2-benzoyl-4-(trifluoromethoxy)phenyl]carbamoyl]-2-methyl-propyl]carbamate

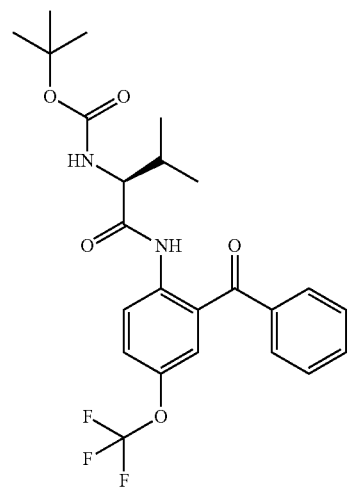

The product was prepared in the same manner as in example 1a) using (2-amino-5-(trifluoromethoxy)phenyl)(phenyl)methanone (300 mg, 1.07 mmol, Eq: 1.00) and (S)-2-(tert-butoxycarbonylamino)-3-methylbutanoic acid (232 mg, 1.07 mmol, Eq: 1.00) as starting materials affording tert-butyl N-[(1S)-1-[[2-benzoyl-4-(trifluoromethoxy)phenyl]carbamoyl]-2-methyl-propyl]carbamate (445 mg, 86.8% yield) as a yellow viscous oil. MS: m/z (M+H)+=481.2 b) (S)-3-Isopropyl-5-phenyl-7-trifluoromethoxy-1,3-dihydro-benzo[e][1,4]diazepin-2-one

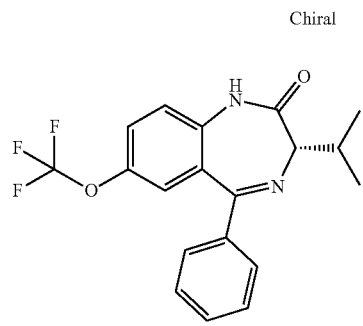 [SMILES: CC(C)[C@@H]1N=C(c2ccccc2)c2cc(OC(F)(F)F)ccc2NC1=O]

The product was prepared in the same manner as in example 1b) using (S)-tert-butyl 1-(2-benzoyl-4-(trifluoromethoxy)phenylamino)-3-methyl-1-oxobutan-2-ylcarbamate (445 mg, 926 μma Eq: 1.00) as starting material affording (S)-3-Isopropyl-5-phenyl-7-trifluoromethoxy-1,3-dihydro-benzo[e][1,4]diazepin-2-one (140 mg, 41.7% yield) as a white solid. MS: m/z (M+H)+=363.2 c) (S)-3-Isopropyl-5-phenyl-7-trifluoromethoxy-1,3-dihydro-benzo[e][1,4]diazepine-2-thione The product was prepared in the same manner as in example 1c) using (S)-3-isopropyl-5-phenyl-7-(trifluoromethoxy)-1H-benzo[e][1,4]diazepin-2(3H)-one (130 mg, 359 μma Eq: 1.00) as starting material affording example 25 (116 mg, 85.4% yield) as yellow solid. MS: m/z (M+H)+=379.1

Example 26

7-chloro-3-(1-hydroxy-1-methyl-ethyl)-5-phenyl-1,3-dihydro-1,4-benzodiazepine-2-thione a) 2-[(7-chloro-5-phenyl-3H-1,4-benzodiazepin-2-yl)sulfanylmethoxy]ethyl-trimethyl-silane and 7-chloro-5-phenyl-1-(2-trimethylsilylethoxymethyl)-3H-1,4-benzodiazepine-2-thione

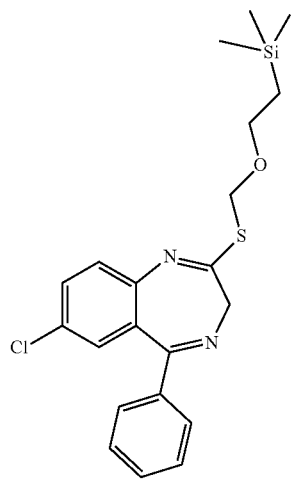

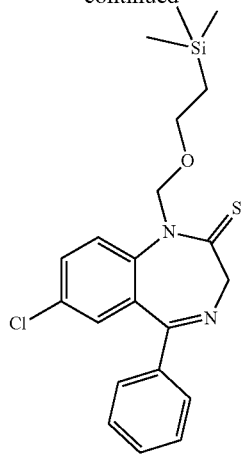

7-chloro-5-phenyl-1H-benzo[e][1,4]diazepine-2(3H)-thione (300 mg, 1.05 mmol, Eq: 1.00) was stirred in THF (6 ml) and cooled in an icebath. sodium hydride 60% in mineral oil (83.7 mg, 2.09 mmol, Eq: 2) was added in one portion (not completely solved). Stirring was continued for 30 min. (2-(chloromethoxy)ethyl)trimethylsilane (388 mg, 412 μl, 2.09 mmol, Eq: 2) was added in one portion (still not completely solved). Stirring was continued over weekend while warming up to room temperature. LCMS/TLC showed new product build. Water was added and extracted three times with ethyl acetate, dried over magnesium sulfate, filtered and evaporated. The cured material was applied on silica gel and purified by column chromatography using heptane/ethyl acetate (0-25% ethyl acetate) as eluent affording a mixture of 2-[(7-chloro-5-phenyl-3H-1,4-benzodiazepin-2-yl)sulfanylmethoxy]ethyl-trimethyl-silane and 7-chloro-5-phenyl-1-(2-trimethylsilylethoxymethyl)-3H-1,4-benzodiazepine-2-thione (210 mg, 48.1%) as light yellow oil. MS: m/z (M+H)+=417.22 b) 2-[7-Chloro-5-phenyl-2-(2-trimethylsilanyl-ethoxymethylsulfanyl)-3H-benzo[e][1,4]diazepin-3-yl]-propan-2-ol

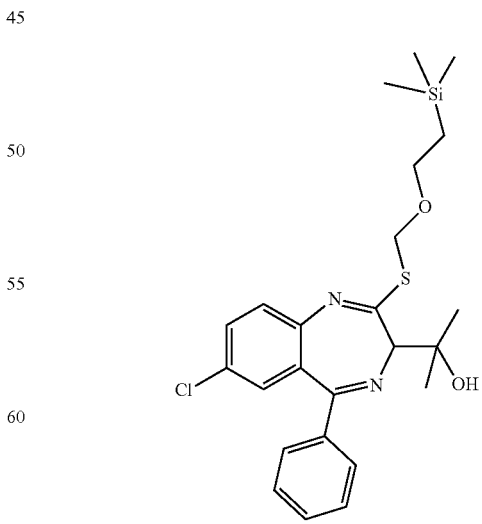

To a solution of diisopropylamine (58.2 mg, 82.0 μl, 575 μmol, Eq: 1.2) in tetrahydrofuran (2.5 ml) was added n-BuLi (360 µl, 575 µmol, Eq: 1.2) at −20° C. under argon atmosphere. The mixture was allowed to warm to 0° C. and was then stirred for 20 minutes, then the mixture was cooled to −78° C. and a solution of 7-chloro-5-phenyl-1-((2-(trimethylsilyl)ethoxy)methyl)-1H-benzo[e][1,4]diazepine-2(3H)-thione (200 mg, 480 µmol, Eq: 1.00) in tetrahydrofuran (2.5 ml) was added dropwise. the mixture turned blue immediately to dark red. After the addition was completed the resulting mixture was stirred for 1 hour at −78° C. Then acetone (83.6 mg, 106 µl, 1.44 mmol, Eq: 3) was added, the mixture turned red and stirring at −78° C. was continued for further 3 hours. TLC showed new spot and lot of starting material left. Stirring was continued for 1 h. Water was added and extracted three times with ethyl acetate, dried over magnesium sulfate, filtered and evaporated. The crude material was applied on silica gel and purified by column chromatography using heptane/ethyl acetate (0-25% ethyl acetate) as eluent affording 2-[7-Chloro-5-phenyl-2-(2-trimethylsilanyl-ethoxymethylsulfanyl)-3H-benzo[e][1,4]diazepin-3-yl]-propan-2-ol (74 mg, 32.5%) as orange oil. MS: m/z (M+H)+=475.17 c) 7-chloro-3-(1-hydroxy-1-methyl-ethyl)-5-phenyl-1,3-dihydro-1,4-benzodiazepine-2-thione 2-(7-chloro-5-phenyl-2-((2-(trimethylsilyl)ethoxy)methylthio)-3H-benzo[e][1,4]diazepin-3-yl)propan-2-ol (60 mg, 126 µmol, Eq: 1.00) was stirred with tribromoborane (278 µl, 278 Eq: 2.2) in Dichloromethane (1.2 ml) for 10 min. LCMS showed just product peak. Water was added and extracted three times with ethyl acetate, dried over magnesium sulfate, filtered and evaporated. The crude material was applied on silica gel and purified by column chromatography using heptane/ethyl acetate as eluent affording example 26 (22 mg, 50.5%) as white solid. MS: m/z (M+H)+=345.0818

Example 27

(3S)-7-Chloro-5-(2-fluorophenyl)-3-isobutyl-1,3-dihydro-1,4-benzodiazepine-2-thione a) tert-butyl N-[(1S)-1-[[4-chloro-2-(2-fluorobenzoyl)phenyl]carbamoyl]-3-methyl-butyl]carbamate

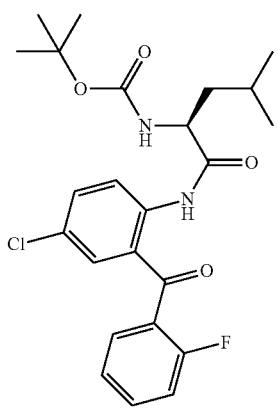 [SMILES: CC(C)C[C@H](NC(=O)OC(C)(C)C)C(=O)Nc1ccc(Cl)cc1C(=O)c1ccccc1F]

The product was prepared in the same manner as in example 1a) using (2-amino-5-chlorophenyl)(2-fluorophenyl)methanone (300 mg, 1.2 mmol, Eq: 1.00) and (S)-2-(tert-butoxycarbonylamino)-4-methylpentanoic acid (278 mg, 1.2 mmol, Eq: 1.00) as starting materials affording tert-butyl N-[(1S)-1-[[4-chloro-2-(2-fluorobenzoyl)phenyl]carbamoyl]-3-methyl-butyl]carbamate (448 mg, 80.5% yield) as a yellow waxy solid. MS: m/z (M−H)−=461.2 b) (S)-7-Chloro-5-(2-fluoro-phenyl)-3-phenyl-1,3-dihydro-benzo[e][1,4]diazepin-2-one

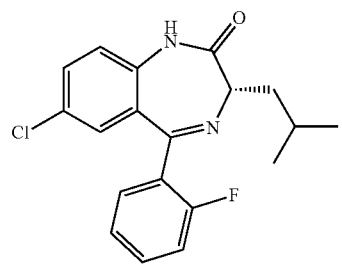

The product was prepared in the same manner as in example 1b) using (S)-tert-butyl (4-chloro-2-(2-fluorobenzoyl)phenylamino)-4-methyl-1-oxopentan-2-ylcarbamate (448 mg, 968 Eq: 1.00) as starting material affording (S)-7-Chloro-5-(2-fluoro-phenyl)-3-phenyl-1,3-dihydro-benzo[e][1,4]diazepin-2-one (315 mg, 94.4% yield) as an orange foam. MS: m/z (M+H)+=345.1 c) (S)-7-Chloro-5-(2-fluoro-phenyl)-3-isobutyl-1,3-dihydro-benzo[e][1,4]diazepine-2-thione The product was prepared in the same manner as in example 1c) using (S)-7-chloro-5-(2-fluorophenyl)-3-isobutyl-1H-benzo[e][1,4]diazepin-2(3H)-one (305 mg, 885 µmol, Eq: 1.00) as starting material affording example 27 (39.0 mg, 12.2% yield) as a yellow foam. MS: m/z (M+H)+=361.1

Example 28

3-[(3,4-Dichlorophenyl)methyl]-5-phenyl-1,3-dihydro-1,4-benzodiazepine-2-thione

The product was prepared in same manner as example 29a, affording example 28 (460 mg) as a light yellow solid.

Example 29

(3S)-7-Chloro-5-(2-fluorophenyl)-3-phenyl-1,3-dihydro-1,4-benzodiazepine-2-thione a) tert-butyl N-[(1S)-2-[4-chloro-2-(2-fluorobenzoyl)anilino]-2-oxo-1-phenyl-ethyl]carbamate

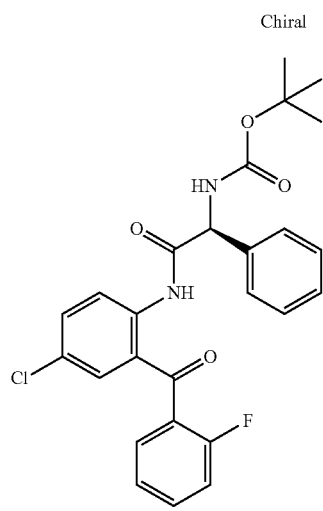 [SMILES: CC(C)(C)OC(=O)N[C@H](C(=O)Nc1ccc(Cl)cc1C(=O)c1ccccc1F)c1ccccc1]

The product was prepared in the same manner as in example 1a) using (2-amino-5-chlorophenyl)(2-fluorophenyl)methanone (300 mg, 1.2 mmol, Eq: 1.00) and (S)-2-(tert-butoxycarbonylamino)-2-phenylacetic acid (302 mg, 1.2 mmol, Eq: 1.00) as starting materials affording tert-butyl N-[(1S)-2-[4-chloro-2-(2-fluorobenzoyl)anilino]-2-oxo-1-phenyl-ethyl]carbamate (474 mg, 81.7% yield) as a brown oil. MS: m/z (M+H)+=483.2 b) (S)-7-Chloro-5-(2-fluoro-phenyl)-3-phenyl-1,3-dihydro-benzo[e][1,4]diazepin-2-one

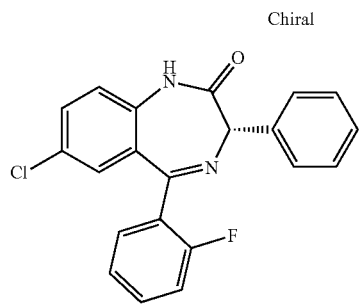 [SMILES: O=C1Nc2ccc(Cl)cc2C(c2ccccc2F)=N[C@H]1c1ccccc1]

The product was prepared in the same manner as in example 1b) using (S)-tert-butyl 2-(4-chloro-2-(2-fluorobenzoyl)phenylamino)-2-oxo-1-phenylethylcarbamate (474 mg, 982 µmol, Eq: 1.00) as starting material affording (S)-7-Chloro-5-(2-fluoro-phenyl)-3-phenyl-1,3-dihydro-benzo[e][1,4]diazepin-2-one (103 mg, 28.8% yield) as a white solid. MS: m/z (M+H)+=365.1 c) (S)-7-Chloro-5-(2-fluoro-phenyl)-3-phenyl-1,3-dihydro-benzo[e][1,4]diazepine-2-thione The product was prepared in the same manner as in example 1c) using (S)-7-chloro-5-(2-fluorophenyl)-3-phenyl-1H-benzo[e][1,4]diazepin-2(3H)-one (103 mg, 282 µmol, Eq: 1.00) as starting material affording example 29 (54 mg, 50.2% yield) as a light yellow solid. MS: m/z (M+H)+=381.1

Example 30

(3S)-3-Benzyl-7-chloro-5-phenyl-1,3-dihydro-1,4-benzodiazepine-2-thione

The product was prepared in same manner as example 29, affording example 30 as first eluting (+) isomer (21 mg, 19.1% yield) as a white solid. MS: m/z (M+H)+=377.0883

Example 31

7-chloro-3,5-diphenyl-1,3-dihydro-1,4-benzodiazepine-2-thione

The product was prepared in the same manner as in example 1c) using 7-chloro-3,5-diphenyl-1H-benzo[e][1,4]diazepin-2(3H)-one (163 mg, 470 µmol, Eq: 1.00) as starting material affording example 31 (69 mg, 40.5% yield) as a light yellow foam. MS: m/z (M+H)+=363.1

Example 32

(3S)-7-bromo-3-isopropyl-5-(3-pyridyl)-1,3-dihydro-1,4-benzodiazepine-2-thione a) tert-butyl N-[(1S)-1-[[2-(2-fluorobenzoyl)-4-methyl-phenyl]carbamoyl]-2-methyl-propyl]carbamate

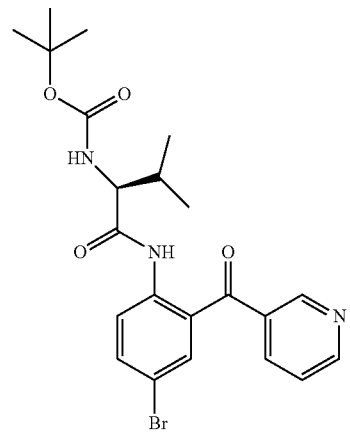

The product was prepared in the same manner as in example 1a) using (2-amino-5-bromophenyl)(pyridin-3-yl)methanone (150 mg, 541 µmol, Eq: 1) and (S)-2-((tert-butoxycarbonyl)amino)-3-methylbutanoic acid (118 mg, 541 µmol, Eq: 1) as starting materials affording tert-butyl N-[(1S)-1-[[2-(2-fluorobenzoyl)-4-methyl-phenyl]carbamoyl]-2-methyl-propyl]carbamate (141 mg, 54% yield) as a light yellow foam. MS: m/z (M+H)+=476.3 b) (3S)-5-(2-fluorophenyl)-3-isopropyl-7-methyl-1,3-dihydro-1,4-benzodiazepin-2-one

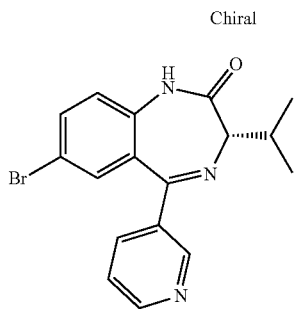 [SMILES: CC(C)[C@@H]1N=C(c2cccnc2)c2cc(Br)ccc2NC1=O]

The product was prepared in the same manner as in example 1b) using (S)-tert-butyl (1-((4-bromo-2-nicotinoylphenyl)amino)-3-methyl-1-oxobutan-2-yl)carbamate (141 mg, 296 µmol, Eq: 1) as starting material affording (3S)-5-(2-fluorophenyl)-3-isopropyl-7-methyl-1,3-dihydro-1,4-benzodiazepin-2-one (64 mg, 60.4% yield) as a yellow solid. MS: m/z (M+H)+=358.1 c) (3S)-7-bromo-3-isopropyl-5-(3-pyridyl)-1,3-dihydro-1,4-benzodiazepine-2-thione The product was prepared in the same manner as in example 5c) using (S)-7-bromo-3-isopropyl-5-(pyridin-3-yl)-1H-benzo[e][1,4]diazepin-2(3H)-one (64 mg, 179 µmol, Eq: 1) as starting material affording example 32 (24.3 mg, 36.3%) as a yellow amorphous. MS: m/z (M+H)+=376.1

Example 33

(3S)-7-chloro-3-(2-methylsulfanylethyl)-5-phenyl-1,3-dihydro-1,4-benzodiazepine-2-thione The product was prepared in the same manner as in example 1c) using (S)-7-chloro-3-(2-(methylthio)ethyl)-5-phenyl-1H-benzo[e][1,4]diazepin-2(3H)-one (100 mg, 290 µmol, Eq: 1.00) as starting material affording example 33 (59 mg, 56.4%) as a light yellow solid. MS: m/z (M+H)+=361.1

Example 34

(3R)-7-chloro-5-(2-fluorophenyl)-3-isopropyl-1,3-dihydro-1,4-benzodiazepine-2-thione a) tert-butyl N-[(1R)-1-[[4-chloro-2-(2-fluorobenzoyl)phenyl]carbamoyl]-2-methyl-propyl]carbamate

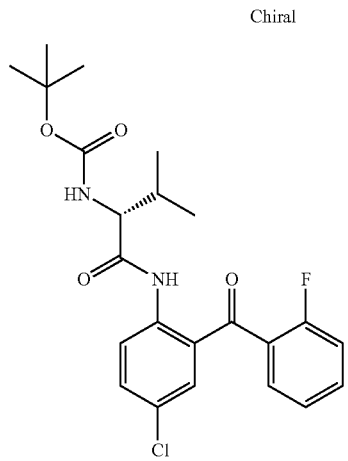 [SMILES: CC(C)[C@@H](NC(=O)OC(C)(C)C)C(=O)Nc1ccc(Cl)cc1C(=O)c1ccccc1F]

The product was prepared in the same manner as in example 1a) using (2-amino-5-chlorophenyl)(2-fluorophenyl)methanone (200 mg, 801 µmol, Eq: 1.00) and (R)-2-(tert-butoxycarbonylamino)-3-methylbutanoic acid (174 mg, 801 µmol, Eq: 1.00) as starting materials affording tert-butyl N-[(1R)-1-[[4-chloro-2-(2-fluorobenzoyl)phenyl]carbamoyl]-2-methyl-propyl]carbamate (309 mg, 85.9% yield) as a yellow viscous oil. MS: m/z (M+H)+=449.2 b) (R)-7-Chloro-5-(2-fluoro-phenyl)-3-isopropyl-1,3-dihydro-benzo[e][1,4]diazepin-2-one

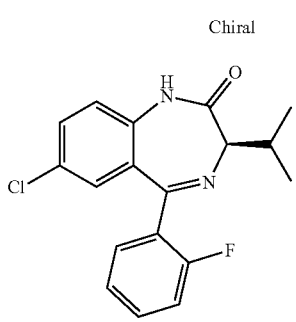 [SMILES: CC(C)[C@H]1N=C(c2ccccc2F)c2cc(Cl)ccc2NC1=O]

The product was prepared in the same manner as in example 1b) using (R)-tert-butyl 1-(4-chloro-2-(2-fluorobenzoyl)phenylamino)-3-methyl-1-oxobutan-2-ylcarbamate (300 mg, 668 µmol, Eq: 1.00) as starting material affording (R)-7-Chloro-5-(2-fluoro-phenyl)-3-isopropyl-1,3-dihydro-benzo[e][1,4]diazepin-2-one (173 mg, 78.3% yield) as a light yellow solid. MS: m/z (M+H)+=331.1 c) (R)-7-Chloro-5-(2-fluoro-phenyl)-3-isopropyl-1,3-dihydro-benzo[e][1,4]diazepine-2-thione The product was prepared in the same manner as in example 1c) using (R)-7-chloro-5-(2-fluorophenyl)-3-isopropyl-1H-benzo[e][1,4]diazepin-2(3H)-one (173 mg, 523 µmol, Eq: 1.00) as starting material affording example 34 (104 mg, 57.3% yield) as a yellow foam. MS: m/z (M+H)+=347.1

Example 35

(3R)-7-chloro-3-isopropyl-5-phenyl-1,3-dihydro-1,4-benzodiazepine-2-thione

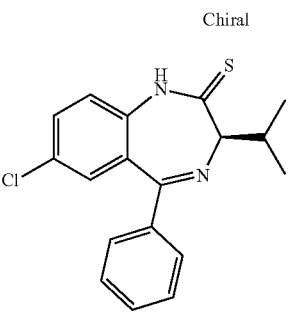 [SMILES: CC(C)[C@H]1N=C(c2ccccc2)c2cc(Cl)ccc2NC1=S]

a) (3R)-7-chloro-3-isopropyl-5-phenyl-1,3-dihydro-1,4-benzodiazepin-2-one

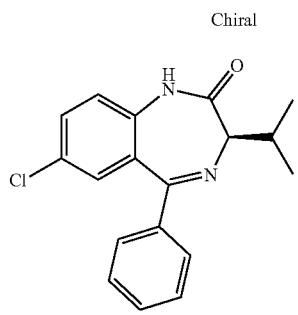 [SMILES: CC(C)[C@H]1N=C(c2ccccc2)c2cc(Cl)ccc2NC1=O]

7-chloro-3-isopropyl-5-phenyl-1H-benzo[e][1,4]diazepin-2(3H)-one (106 mg, 339 µmol, Eq: 1.00) was submitted to chiral HPLC separation affording (3R)-7-chloro-3-isopropyl-5-phenyl-1,3-dihydro-1,4-benzodiazepin-2-one (43 mg, 40.6% yield) as a white amorphous. MS: m/z (M+H)+=313.1 b) (R)-7-Chloro-3-isopropyl-5-phenyl-1,3-dihydro-benzo[e][1,4]diazepine-2-thione The product was prepared in the same manner as in example 1c) using (R)-7-chloro-3-isopropyl-5-phenyl-1H-benzo[e][1,4]diazepin-2(3H)-one (46 mg, 147 µmol, Eq: 1.00) as starting material affording example 35 (30 mg, 62.0% yield) as a light yellow solid. MS: m/z (M+H)+=329.1

Example 36

(S)-7-Chloro-3-isobutyl-5-phenyl-1,3-dihydro-benzo[e][1,4]diazepine-2-thione a) tert-butyl N-[(1S)-1-[(2-benzoyl-4-chloro-phenyl)carbamoyl]-3-methyl-butyl]carbamate

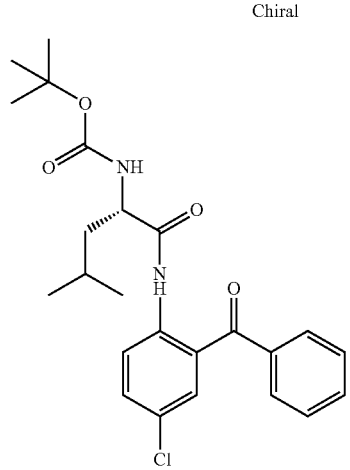 [SMILES: CC(C)C[C@H](NC(=O)OC(C)(C)C)C(=O)Nc1ccc(Cl)cc1C(=O)c1ccccc1]

The product was prepared in the same manner as in example 1a) using (2-amino-5-chlorophenyl)(phenyl)methanone (500 mg, 2.16 mmol, Eq: 1.00) and (S)-2-(tert-butoxycarbonylamino)-4-methylpentanoic acid (499 mg, 2.16 mmol, Eq: 1.00) as starting materials affording tert-butyl N-[(1S)-1-[(2-benzoyl-4-chloro-phenyl)carbamoyl]-3-methyl-butyl]carbamate (875 mg, 91.1% yield) as a yellow solid. MS: m/z (M+H)+=445.2 b) (S)-7-Chloro-3-isobutyl-5-phenyl-1,3-dihydro-benzo[e][1,4]diazepin-2-one

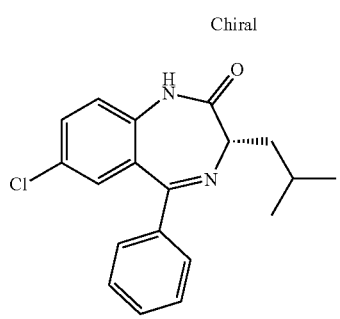 [SMILES: CC(C)C[C@@H]1N=C(c2ccccc2)c2cc(Cl)ccc2NC1=O]

The product was prepared in the same manner as in example 1b) using (S)-tert-butyl 1-(2-benzoyl-4-chlorophenylamino)-4-methyl-1-oxopentan-2-ylcarbamate (875 mg, 1.97 mmol, Eq: 1.00) as starting material affording (S)-7-Chloro-3-isobutyl-5-phenyl-1,3-dihydro-benzo[e][1,4]diazepin-2-one (619 mg, 96.3% yield) as a light yellow foam. MS: m/z (M+H)+=327.2 c) (S)-7-Chloro-3-isobutyl-5-phenyl-1,3-dihydro-benzo[e][1,4]diazepine-2-thione The product was prepared in the same manner as in example 1c) using (S)-7-chloro-3-isobutyl-5-phenyl-1H-benzo[e][1,4]diazepin-2(3H)-one (300 mg, 918 µmol, Eq: 1.00) as starting material affording example 36 (141 mg, 44.8% yield) as a light yellow foam. MS: m/z (M+H)+=343.1

Example 37

7-amino-3-ethyl-5-(2-fluorophenyl)-1,3-dihydro-1,4-benzodiazepine-2-thione a) 3-ethyl-5-(2-fluorophenyl)-7-nitro-1,3-dihydro-1,4-benzodiazepine-2-thione

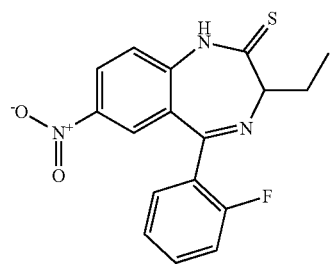

The product was prepared in the same manner as in example 5c) using 3-ethyl-5-(2-fluorophenyl)-7-nitro-1H-benzo[e][1,4]diazepin-2(3H)-one (150 mg, 458 µmol, Eq: 1) as starting material affording 3-ethyl-5-(2-fluorophenyl)-7- nitro-1,3-dihydro-1,4-benzodiazepine-2-thione (19.1 mg, 12.1%) as a yellow solid. MS: m/z (M+H)+=344.1 b) 7-amino-3-ethyl-5-(2-fluorophenyl)-1,3-dihydro-1,4-benzodiazepine-2-thione tin (II) chloride dihydrate (33.1 mg, 147 µmol, Eq: 3.36) was added to a solution of 3-ethyl-5-(2-fluorophenyl)-7-nitro-1H-benzo[e][1,4]diazepine-2(3H)-thione (15 mg, 43.7 µmol, Eq: 1) in DMF (300 µL) at room temperature. The mixture was stirred at room temperature overnight. Not complete. After stirring over an additional night the reaction was complete. The solvent was evaporated and some methanol was added, applied on silica gel and purified by column chromatography using heptane/ethyl acetate (0-40% ethyl acetate) as eluent affording example 37 (10 mg, 73%) as an off-white solid. MS: m/z (M+H)+=329.2

Example 38

7-chloro-3-(1-methoxyethyl)-5-phenyl-1,3-dihydro-1,4-benzodiazepine-2-thione

The product was prepared in the same manner as in example 5 using 7-chloro-3-(1-methoxyethyl)-5-phenyl-1H-benzo[e][1,4]diazepin-2(3H)-one (60 mg, 182 µmol, Eq: 1.00) as starting material affording example 38 (13 mg, 20.7%) as a light yellow oil. MS: m/z (M+H)+=345.1

Example 39

(3S)-7-chloro-5-cyclohexyl-3-isopropyl-1,3-dihydro-1,4-benzodiazepine-2-thione a) tert-butyl N-[(1R)-1-[[4-chloro-2-(cyclohexanecarbonyl)phenyl]carbamoyl]-2-methyl-propyl]carbamate

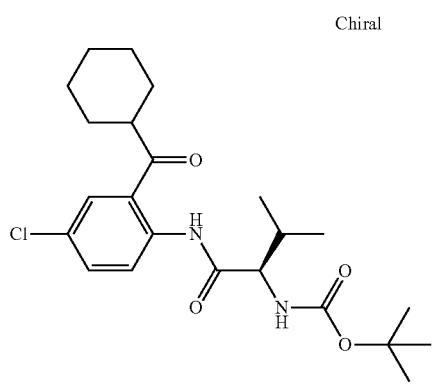 [SMILES: CC(C)[C@@H](NC(=O)OC(C)(C)C)C(=O)Nc1ccc(Cl)cc1C(=O)C1CCCCC1]

Chiral

The product was prepared in the same manner as in example 1a) using (2-amino-5-chlorophenyl)(cyclohexyl)methanone (173.6 mg, 730 µmol, Eq: 1) and (S)-2-((tert-butoxycarbonyl)amino)-3-methylbutanoic acid (159 mg, 730 µmol, Eq: 1) as starting materials affording tert-butyl N-[(1R)-1-[[4-chloro-2-(cyclohexanecarbonyl)phenyl]carbamoyl]-2-methyl-propyl]carbamate (171 mg, 53.6% yield) as a yellow solid. MS: m/z ([M−BOC]+H)+=337.2 b) (3S)-7-chloro-5-cyclohexyl-3-isopropyl-1,3-dihydro-1,4-benzodiazepin-2-one

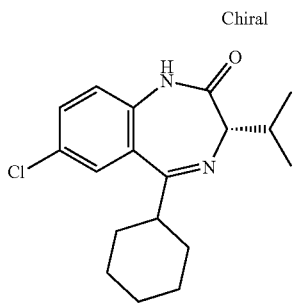 [SMILES: CC(C)[C@@H]1N=C(C2CCCCC2)c2cc(Cl)ccc2NC1=O]

Chiral

The product was prepared in the same manner as in example 1b) using (R)-tert-butyl (1-((4-chloro-2-(cyclohexanecarbonyl)phenyl)amino)-3-methyl-1-oxobutan-2-yl)carbamate (171 mg, 391 µmol, Eq: 1) as starting material affording (3S)-7-chloro-5-cyclohexyl-3-isopropyl-1,3-dihydro-1,4-benzodiazepin-2-one (81 mg, 64.9% yield) as a white solid. MS: m/z (M+H)+=319.2 c) (3S)-7-chloro-5-cyclohexyl-3-isopropyl-1,3-dihydro-1,4-benzodiazepine-2-thione The product was prepared in the same manner as in example 1c) using (S)-7-chloro-5-cyclohexyl-3-isopropyl-1H-benzo[e][1,4]diazepin-2(3H)-one (81 mg, 254 µmol, Eq: 1) as starting material affording example 39 (5 mg, 5.88% yield) as a light yellow solid. MS: m/z (M+H)+=335.1

Example 40

(3S)-3-isopropyl-7-methoxy-5-phenyl-1,3-dihydro-1,4-benzodiazepine-2-thione a) tert-butyl N-[(1S)-1-[(2-benzoyl-4-methoxy-phenyl)carbamoyl]-2-methyl-propyl]carbamate

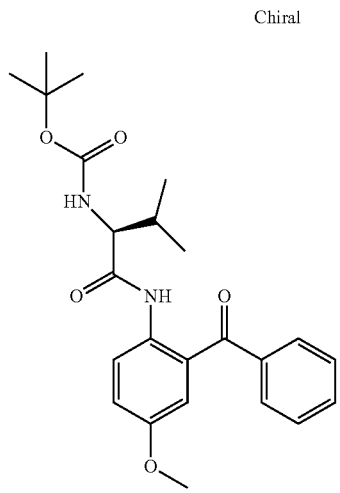 [SMILES: COc1ccc(NC(=O)[C@@H](NC(=O)OC(C)(C)C)C(C)C)c(C(=O)c2ccccc2)c1]

Chiral

The product was prepared in the same manner as in example 1a) using (2-amino-5-methoxyphenyl)(phenyl)methanone (207 mg, 911 μmol, Eq: 1) and (S)-2-((tert-butoxycarbonyl)amino)-3-methylbutanoic acid (198 mg, 911 μmol, Eq: 1) as starting materials affording tert-butyl N-[(1S)-1-[(2-benzoyl-4-methoxy-phenyl)carbamoyl]-2-methyl-propyl]carbamate (170 mg, 43.8% yield) as a yellow oil. MS: m/z ([M+H]+=427.3 b) (3S)-3-isopropyl-7-methoxy-5-phenyl-1,3-dihydro-1,4-benzodiazepin-2-one

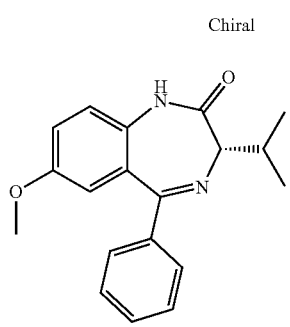 [SMILES: COc1ccc2c(c1)C(c1ccccc1)=N[C@@H](C(C)C)C(=O)N2]

Chiral

The product was prepared in the same manner as in example 1b) using (S)-tert-butyl (1-((2-benzoyl-4-methoxyphenyl)amino)-3-methyl-1-oxobutan-2-yl)carbamate (170 mg, 399 μmol, Eq: 1) as starting material affording (3S)-3-isopropyl-7-methoxy-5-phenyl-1,3-dihydro-1,4-benzodiazepin-2-one (51 mg, 41.5% yield) as a white solid. MS: m/z (M+H)+=309.2 c) (3S)-3-isopropyl-7-methoxy-5-phenyl-1,3-dihydro-1,4-benzodiazepine-2-thione The product was prepared in the same manner as in example 1c) using (S)-3-isopropyl-7-methoxy-5-phenyl-1H-benzo[e][1,4]diazepin-2(3H)-one (51 mg, 165 μmol, Eq: 1) as starting material affording example 40 (25 mg, 46.6% yield) as a white solid. MS: m/z (M+H)+=325.2

Example 41

3-methyl-5-phenyl-1,3-dihydro-1,4-benzodiazepine-2-thione

The product was prepared in the same manner as in example 5c) using 3-methyl-5-phenyl-1H-benzo[e][1,4]diazepin-2(3H)-one (150 mg, 599 μmol, Eq: 1.00) as starting material affording example 41 (141 mg, 88.3% yield) as an off-white solid. MS: m/z (M+H)+=267.2

Example 42

7-chloro-3-ethyl-5-phenyl-1,3-dihydro-1,4-benzodiazepine-2-thione a) tert-butyl N-[(tert-butoxy) carbonyl]-N-(4-chloro-2-nitrophenyl) carbamate

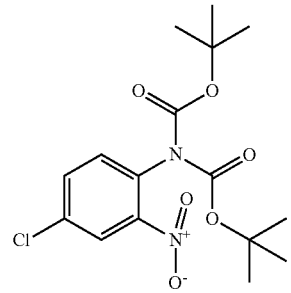 [SMILES: CC(C)(C)OC(=O)N(C(=O)OC(C)(C)C)c1ccc(Cl)cc1[N+](=O)[O-]]

To a solution of 4-chloro-2-nitroaniline (4 g, 23.25 mmol) and di-tert-butyl dicarbonate (11.78 mL) in THF (40 ml) was added, followed by 4-dimethylaminopyridine (20 mg) at 25° C. The mixture was stirred for 6 h at 90° C. After completion of reaction (monitored by TLC), the reaction mixture was cooled to ambient temperature, concentrated under reduced pressure and the crude residue was purified by washing with pentane to give tert-butyl N-[(tert-butoxy) carbonyl]-N-(4-chloro-2-nitrophenyl) carbamate (5 g, 58%) as a white solid. MS: m/z (M+H)+=373.3 (M+1).

b) tert-butyl N-(2-amino-4-chlorophenyl)-N-[(tert-butoxy) carbonyl]carbamate

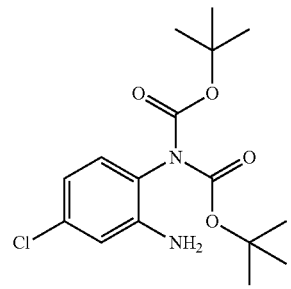 [SMILES: CC(C)(C)OC(=O)N(C(=O)OC(C)(C)C)c1ccc(Cl)cc1N]

To a solution of tert-butyl N-[(tert-butoxy) carbonyl]-N-(4-chloro-2-nitrophenyl) carbamate (5 g, 13.44 mmol) in mixture of ethanol (50 ml) and water (50 ml) was added Zn dust (13.18 g, 201.6 mmol) followed by ammonium chloride (5.7 g, 107.5 mmol). The reaction mixture was stirred at 25° C. for 16 h. The reaction mixture was filtered through a bed of celite and concentrated under reduced pressure. The crude residue was purified by flash chromatography (silicagel) using 30% ethyl acetate/hexane affording tert-butyl N-(2-amino-4-chlorophenyl)-N-[(tert-butoxy) carbonyl]carbamate as yellow solid (4 g, 86%). MS: m/z (M+H)+=343.1.

c) ethyl 2-formylbutanoate

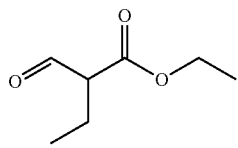

A solution of ethyl butanoate (5 g, 43.04 mmol) in dichloromethane (30 ml) was added slowly ethyl formate (7 ml, 86 mmol) followed by titanium tetrachloride (9.5 ml) at 0° C. The mixture was stirred for 5 min at 0° C. After that triethylamine (15 ml, 107.6 mmol) was added and the reaction mixture was stirred at 0° C. for 1 h, warmed at 25° C. and stirred for another hour. After completion of reaction, water (200 ml) was added and extracted with ethyl acetate (2×300 ml), the separated organic layers were washed with brine (100 ml) and dried over sodium sulfate, filtered and concentrated. The residue was purified by vacuum distillation to get ethyl 2-formylbutanoate as yellow liquid (3 g, 21 mmol). This material was used without further purification.

d) ethyl 2-{[(2-{bis [(tert-butoxy) carbonyl]amino}-5-chlorophenyl)amino]methyl}butanoate

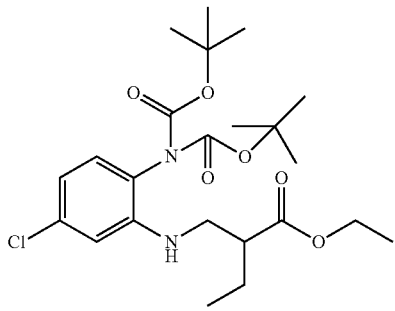 [SMILES: CCOC(=O)C(CC)CNc1cc(Cl)ccc1N(C(=O)OC(C)(C)C)C(=O)OC(C)(C)C]

A solution of tert-butyl N-(2-amino-4-chlorophenyl)-N-[(tert-butoxy) carbonyl]carbamate (2 g, 5.8 mmol) in ethanol (30 ml) was added slowly ethyl 2-formylbutanoate (1.2 g, 8.7 mmol) followed by acetic acid (0.6 ml) and molecular sieves. The mixture was stirred for 4 h at 25° C. After that sodium cyanoborohydride (0.74 g 11.69 mmol) was added and reaction mixture was heated for 16 h to 65° C. After completion the reaction was cooled to 25° C., quenched by addition of ammonium bicarbonate (30 ml) and solvent was removed under reduced pressure. Water (100 ml) was added and extracted with ethyl acetate (2×150 ml), the organic layers were separated, washed with brine (100 ml) and dried over sodium sulfate, filtered and concentrated. The crude residue was purified by combiflash column chromatography eluting with 20% ethyl acetate/hexane to afford ethyl 2-{[(2-{bis [(tert-butoxy) carbonyl]amino}-5-chlorophenyl) amino]methyl}butanoate as yellow liquid (660 mg, 24%). MS: m/z (M+H)+=471.0.

e) ethyl 2-{[(2-amino-5-chlorophenyl) amino]methyl}butanoate

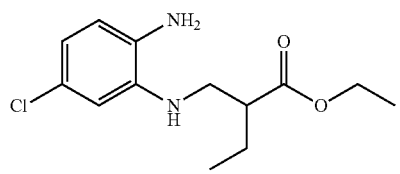 [SMILES: CCOC(=O)C(CC)CNc1cc(Cl)ccc1N]

To a solution of ethyl 2-{[(2-{bis [(tert-butoxy)carbonyl] amino}-5-chlorophenyl)amino]methyl}butanoate (1 g, 2.12 mmol) in dichloromethane (15 ml) was slowly added 4M hydrochloric acid in dioxane at 0° C. The reaction mixture was allowed to warm to 25° C. and stirred for 4 h. The volatiles were removed under reduced pressure, the crude residue was diluted with water (100 ml), and the aqueous layer was neutralized with a saturated aqueous solution of sodium bicarbonate at 0° C. up to pH~7. The aqueous layer was extracted with ethyl acetate (2×150 ml), the combined organic layer separated and washed with brine (100 ml) and dried over sodium sulfate, filtered and concentrated to afford ethyl 2-{[(2-amino-5-chlorophenyl) amino] methyl}butanoate as yellow liquid (800 mg, crude). MS: m/z (M+H)+=271.0. This material was used for the next step without further purification.

f) 7-chloro-3-ethyl-2,3,4,5-tetrahydro-1H-1,5-benzo-diazepin-2-one

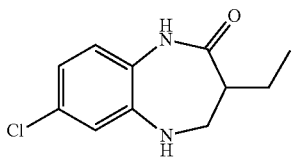

To a solution of ethyl 2-{[(2-amino-5-chlorophenyl) amino]methyl}butanoate (800 mg, 2.96 mmol) in methanol (30 ml) was added sodium methoxide (0.5M in methanol) (16 ml) slowly at 25° C. The reaction mixture was warmed to 60° C. and stirred for 28 h. The volatiles were removed under reduced pressure. Purification by flash chromatography (silicagel) using 20% ethyl acetate/hexane afforded ethyl 2-{[(2-{bis [(tert-butoxy) carbonyl]amino}-5-chlorophenyl) amino]methyl}butanoate7-chloro-3-ethyl-2,3,4,5-tetrahydro-1H-1,5-benzodiazepin-2-one as yellow white solid (130 mg, 20%). MS: m/z (M+H)+=225.3.

g) 7-chloro-3-ethyl-5-phenyl-2,3,4,5-tetrahydro-1H-1,5-benzodiazepin-2-one

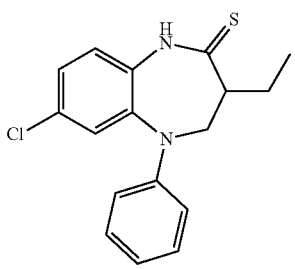 [SMILES: CCC1CN(c2ccccc2)c2cc(Cl)ccc2NC1=S]

To a solution of 7-chloro-3-ethyl-2,3,4,5-tetrahydro-1H-1,5-benzodiazepin-2-one (80 mg, 0.36 mmol) in dimethoxyethane (5 ml) at 25° C. were added bromobenzene (0.06 ml, 0.54 mmol), X-phos (9 mg, 0.02 mmol) and sodium tert-.butoxide (68 mg, 0.72 mmol) and the mixture was purged with argon for 10 min. After that tris(dibenzylideneacetone)dipalladium(0) (33 mg, 0.04 mmol) was added and again purged with argon for another 10 min. The reaction mixture was heated to 60° C. and stirred at this temperature for 6 h. The reaction mixture was allowed to cool to ambient temperature, filtered through bed of celite and washed with ethyl acetate (30 ml). The filtrate was diluted with water (30 ml) and extracted with ethyl acetate (2×50 ml) and the combined organic layers were washed with water (50 ml), brine (50 ml), dried over sodium sulfate and concentrated in vacuo. The crude was purified by column chromatography via amine silica gel eluting with 40% ethyl acetate in hexane to afford 7-chloro-3-ethyl-5-phenyl-2,3,4,5-tetrahydro-1H-1,5-benzodiazepin-2-one as a white solid (65 mg, 65%). This material was used for next step without further purification.

h) 7-chloro-3-ethyl-5-phenyl-2,3,4,5-tetrahydro-1H-1,5-benzodiazepine-2-thione

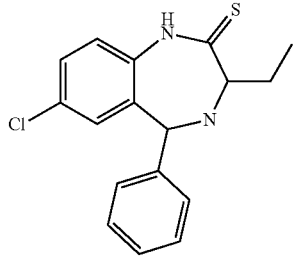 [SMILES: CCC1NC(c2ccccc2)c2cc(Cl)ccc2NC1=S]

A stirred suspension of 7-Chloro-3-ethyl-5-phenyl-2,3,4,5-tetrahydro-1H-1,5-benzodiazepin-2-one (600 mg, 3.17 mmol) in tetrahydrofuran (4 ml) was heated to 40° C. under nitrogen. Lawesson's Reagent (68 mg, 0.17 mmol) was added and the reaction mass was stirred at 60° C. for 4 h. The hot reaction mixture was poured into a mixture of ethyl acetate (25 ml) and water (25 ml) and stirred vigorously. After dilution with water (50 ml) and extraction with ethyl acetate (2×50 ml), the combined organic layers were washed with water (50 ml) and brine (50 ml), dried over sodium sulfate, filtered and concentrated under reduced pressure. Purification by column chromatography via amine silica gel eluting with 30% ethyl acetate in hexane afforded 7-Chloro-3-ethyl-5-phenyl-2,3,4,5-tetrahydro-1H-1,5-benzodiazepine-2-thione as a white solid (24 mg, 45%). MS: m/z (M−H)−=315.3.

Example X1

3-Benzyl-7-chloro-5-(2-chloro-phenyl)-1,3-dihydro-benzo[1,4]diazepine-2-thione

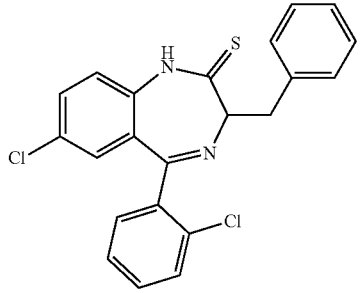 [SMILES: S=C1Nc2ccc(Cl)cc2C(c2ccccc2Cl)=NC1Cc1ccccc1]

The product was prepared in the same manner as in example 5c) using 3-Benzyl-7-chloro-5-(2-chloro-phenyl)-1,3-dihydro-benzo[1,4]diazepine-2-one as starting material affording 3-Benzyl-7-chloro-5-(2-chloro-phenyl)-1,3-dihydro-benzo[1,4]diazepine-2-thione as yellow solid. MS: m/z (M+H)+=411.05, no activity at M1 receptor Example X2

7-chloro-5-(2-chlorophenyl)-3-(cyclopropylmethyl)-1H-benzo[e][1,4]diazepine-2(3H)-thione

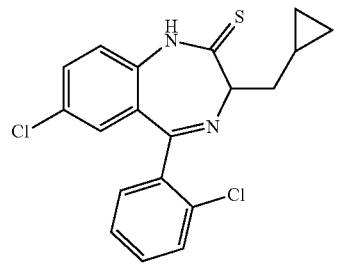 [SMILES: S=C1Nc2ccc(Cl)cc2C(c2ccccc2Cl)=NC1CC1CC1]

7-Chloro-5-(2-chloro-phenyl)-3-cyclopropylmethyl-1,3-dihydro-benzo[e][1,4]diazepine-2-thione A mixture of 7-chloro-5-(2-chlorophenyl)-3-(cyclopropylmethyl)-1H-benzo[e][1,4]diazepin-2(3H)-one (73 mg, 203 µmol) and Lawesson's reagent (164 mg, 406 µmol) in 1,2-dimethoxyethane (3 ml) was stirred for 18 hours at 80° C. in a closed vial. The crude material was purified by flash chromatography over a 20 g silicagel column using heptane/ethyl acetate 10-30% as eluent, affording 7-chloro-5-(2-chlorophenyl)-3-(cyclopropylmethyl)-1H-benzo[e][1,4]diazepine-2(3H)-thione (28 mg, 37% yield) as yellow solid. MS: m/z (M+H)+=373, no activity at M1 receptor

[1] Melancon et al., Drug Discov Today. 2013 December; 18(0)
[2] Simonyi et al, Bioorganic Chemistry 18, 1-12 (1990), 1-12
[3] U.S. Pat. No. 4,031,078
[4] Meguro K. et al, Chem. Pharm. Bull. (Tokyo), 21, 2382 (1973)
[5] U.S. Pat. No. 4,514,407
[6] U.S. Pat. No. 3,987,052
[7] Journal of Heterocyclic Chemistry, 1984, vol. 21, p. 1457-1464

The invention claimed is:
1. A compound of formula I, selected from the group consisting of:
   (3R)-3-benzyl-7-chloro-5-phenyl-1,3-dihydro-1,4-benzodiazepine-2-thione,
   (3R)-7-chloro-3-(2-methylsulfanylethyl)-5-phenyl-1,3-dihydro-1,4-benzodiazepine-2-thione,
   (3R)-7-chloro-3-isopropyl-5-phenyl-1,3-dihydro-1,4-benzodiazepine-2-thione,
   (3R)-7-chloro-5-(2-fluorophenyl)-3-(trifluoromethyl)-1,3-dihydro-1,4-benzodiazepine-2-thione,
   (3R)-7-chloro-5-(2-fluorophenyl)-3-isopropyl-1,3-dihydro-1,4-benzodiazepine-2-thione,
   (3S)-3-benzyl-7-chloro-5-phenyl-1,3-dihydro-1,4-benzodiazepine-2-thione,
   (3S)-3-isopropyl-5,7-diphenyl-1,3-dihydro-1,4-benzodiazepine-2-thione,

(3S)-3-isopropyl-5-phenyl-7-(trifluoromethoxy)-1,3-dihydro-1,4-benzodiazepine-2-thione,
(3S)-3-isopropyl-5-phenyl-7-(trifluoromethyl)-1,3-dihydro-1,4-benzodiazepine-2-thione,
(3S)-3-isopropyl-7-methoxy-5-phenyl-1,3-dihydro-1,4-benzodiazepine-2-thione,
(3S)-5-(2-fluorophenyl)-3-isopropyl-7-methyl-1,3-dihydro-1,4-benzodiazepine-2-thione,
(3S)-7-bromo-3-isopropyl-5-(2-pyridyl)-1,3-dihydro-1,4-benzodiazepine-2-thione,
(3S)-7-bromo-3-isopropyl-5-(3-pyridyl)-1,3-dihydro-1,4-benzodiazepine-2-thione,
(3S)-7-chloro-3-(2-methylsulfanylethyl)-5-phenyl-1,3-dihydro-1,4-benzodiazepine-2-thione,
(3S)-7-chloro-3-(cyclopropylmethyl)-5-phenyl-1,3-dihydro-1,4-benzodiazepine-2-thione,
(3S)-7-chloro-3-cyclopropyl-5-phenyl-1,3-dihydro-1,4-benzodiazepine-2-thione,
(3S)-7-chloro-3-ethyl-5-phenyl-1,3-dihydro-1,4-benzodiazepine-2-thione,
(3S)-7-chloro-3-isobutyl-5-phenyl-1,3-dihydro-1,4-benzodiazepine-2-thione,
(3S)-7-chloro-3-isopropyl-5-phenyl-1,3-dihydro-1,4-benzodiazepine-2-thione,
(3S)-7-chloro-3-methyl-5-phenyl-3-propyl-1H-1,4-benzodiazepine-2-thione,
(3S)-7-chloro-5-(2-fluorophenyl)-3-(trifluoromethyl)-1,3-dihydro-1,4-benzodiazepine-2-thione,
(3S)-7-chloro-5-(2-fluorophenyl)-3-isobutyl-1,3-dihydro-1,4-benzodiazepine-2-thione,
(3S)-7-chloro-5-(2-fluorophenyl)-3-isopropyl-1,3-dihydro-1,4-benzodiazepine-2-thione,
(3S)-7-chloro-5-(2-fluorophenyl)-3-phenyl-1,3-dihydro-1,4-benzodiazepine-2-thione,
(3S)-7-chloro-5-(3-chlorophenyl)-3-isopropyl-1,3-dihydro-1,4-benzodiazepine-2-thione,
(3S)-7-chloro-5-cyclohexyl-3-isopropyl-1,3-dihydro-1,4-benzodiazepine-2-thione,
(3S)-7-chloro-5-phenyl-3-(2,2,2-trifluoroethyl)-1,3-dihydro-1,4-benzodiazepine-2-thione,
(3S)-7-chloro-5-phenyl-3-propyl-1,3-dihydro-1,4-benzodiazepine-2-thione,
(3S)-8-chloro-5-(2-fluorophenyl)-3-isopropyl-1,3-dihydro-1,4-benzodiazepine-2-thione,
[7-chloro-5-(2-fluorophenyl)-2-thioxo-1,3-dihydro-1-benzazepin-3-yl] acetate,
(3S)-5-(4-fluorophenyl)-3-isopropyl-7-(trifluoromethoxy)-1,3-dihydro-1,4-benzodiazepine-2-thione,
3-[(3,4-dichlorophenyl)methyl]-5-phenyl-1,3-dihydro-1,4-benzodiazepine-2-thione,
3-methyl-5-phenyl-1,3-dihydro-1,4-benzodiazepine-2-thione,
3-methyl-7-nitro-5-phenyl-1,3-dihydro-1,4-benzodiazepine-2-thione,
7-amino-3-ethyl-5-(2-fluorophenyl)-1,3-dihydro-1,4-benzodiazepine-2-thione,
7-chloro-3-(1-hydroxy-1-methyl-ethyl)-5-phenyl-1,3-dihydro-1,4-benzodiazepine-2-thione,
7-chloro-3-(1-methoxyethyl)-5-phenyl-1,3-dihydro-1,4-benzodiazepine-2-thione,
7-chloro-3,5-diphenyl-1,3-dihydro-1,4-benzodiazepine-2-thione, and
7-chloro-3-isopropyl-5-phenyl-1,3-dihydro-1,4-benzodiazepine-2-thione,
or a pharmaceutically acceptable salt thereof.

2. A pharmaceutical composition comprising a compound of claim 1 and a pharmaceutically acceptable carrier.

3. A compound selected from the group consisting of 5-cyclohexyl-7-(trifluoromethyl)-1,3-dihydro-1,4-benzodiazepine-2-thione, 7-chloro-5-propyl-1,3-dihydro-1,4-benzodiazepine-2-thione, or a pharmaceutically acceptable salt thereof.

4. A pharmaceutical composition comprising a compound of claim 3 and a pharmaceutically acceptable carrier.

* * * * *

UNITED STATES PATENT AND TRADEMARK OFFICE
CERTIFICATE OF CORRECTION

Page 1 of 1

PATENT NO. : 11,021,448 B2
APPLICATION NO. : 16/399134
DATED : June 1, 2021
INVENTOR(S) : Alexander Flohr It is certified that error appears in the above-identified patent and that said Letters Patent is hereby corrected as shown below:

In the Claims

Column 64, Lines 52-53 please delete:
"A compound of formula I, selected from the group consisting of:"

And insert:
--A compound selected from the group consisting of:--

Signed and Sealed this
Twenty-second Day of March, 2022

Drew Hirshfeld
*Performing the Functions and Duties of the*
*Under Secretary of Commerce for Intellectual Property and*
*Director of the United States Patent and Trademark Office*